(12) United States Patent
Sonoda et al.

(10) Patent No.: US 7,780,610 B2
(45) Date of Patent: Aug. 24, 2010

(54) COMPONENT MEASURING INSTRUMENT AND CHIP

(75) Inventors: Kouichi Sonoda, Kushikino (JP); Hisao Nishikawa, Ashigarakami-gun (JP); Masao Takinami, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1068 days.

(21) Appl. No.: 10/488,311

(22) PCT Filed: Sep. 19, 2001

(86) PCT No.: PCT/JP01/08125

§ 371 (c)(1),
(2), (4) Date: Mar. 3, 2004

(87) PCT Pub. No.: WO03/026506

PCT Pub. Date: Apr. 3, 2003

(65) Prior Publication Data

US 2004/0210247 A1    Oct. 21, 2004

(51) Int. Cl.
*A61B 5/00* (2006.01)
(52) U.S. Cl. .................. 600/583; 600/573; 600/576; 600/584
(58) Field of Classification Search .......... 600/583, 600/573, 576, 578, 584; 606/181, 182
See application file for complete search history.

(56) References Cited

U.S. PATENT DOCUMENTS 4,627,445 A * 12/1986 Garcia et al. ............. 600/583
5,871,494 A    2/1999 Simons
6,210,420 B1   4/2001 Mauze et al.
6,261,245 B1 * 7/2001 Kawai et al. ............. 600/576
7,001,344 B2 * 2/2006 Freeman et al. .......... 600/583

FOREIGN PATENT DOCUMENTS

EP    0 988 828 A    3/2000
EP    1 112 717 A    7/2001
WO    WO 00/40150 A  7/2000

OTHER PUBLICATIONS

Supplemental European Search Report in EP 01 96 7726, dated Nov. 24, 2008.

* cited by examiner

*Primary Examiner*—Max Hindenburg
*Assistant Examiner*—Emily M Lloyd
(74) *Attorney, Agent, or Firm*—Buchanan Ingersoll & Rooney PC

(57) ABSTRACT

It is an object of the present invention to provide a component measuring instrument with which a predetermined component in blood can be measured securely and in a short time. The component measuring instrument, which is used by mounting therein a chip having a puncture needle, includes: a specimen sampling portion application portion to which a specimen sampling portion to be punctured is applied; a puncturer for moving the puncture needle; pressure reducer for putting the punctured portion of the specimen sampling portion punctured by the puncture needle, together with a containing space for the puncture needle, into a reduced-pressure condition; measurer for measuring the amount of a predetermined component in the blood sampled from the punctured portion; and a chip retracting mechanism for moving the chip in a direction away from the specimen sampling portion while maintaining the reduced-pressure condition generated by the pressure reducer.

16 Claims, 18 Drawing Sheets

COMPONENT MEASURING INSTRUMENT AND CHIP

TECHNICAL FIELD

The present invention relates to a component measuring instrument, particularly to a component measuring instrument for sampling blood by puncturing a specimen sampling portion such as a fingertip with a puncture needle and for measuring the amount of a specific component such as glucose in the blood, in examination of the blood. In addition, the present invention relates to a chip to be used in the state of being mounted in the component measuring instrument used for measurement of, for example, blood sugar level.

BACKGROUND ART

In recent years, attendant on the increase in the number of diabetics, self measurement of blood sugar, i.e., monitoring the daily variation of blood sugar level by the patient himself has been recommended.

The measurement of blood sugar level is carried out by use of a blood sugar measuring instrument such that a test paper undergoing coloration according to the amount of blood sugar in blood is mounted, the blood is supplied to and developed on the test paper, and the degree of coloration is optically measured (colorimetry), thereby quantifying the blood sugar level.

As a method for sampling the blood of the patient by himself prior to the measurement, it has been practiced to puncture the skin of a fingertip or the like by use of a puncture device comprising a puncture needle or a small knife, and thereafter to apply a pressure to the surroundings of the punctured portion with a finger or the like, thereby pressing the blood out from the punctured portion.

However, the fingertip principally used as the specimen sampling portion has the following problem. Namely, on one hand the fingertip is suitable for sampling of blood because capillary vessels are concentrated in the fingertip, but, on the other hand, nerves are also concentrated in the fingertip, which causes a pain during blood sampling. Therefore, the sampling of blood from the fingertip exerts heavy pain and burden on the patient, and is accompanied by a fear arising from puncturing, resulting in that many patients cannot continue the self measurement of blood sugar.

In addition, the conventional blood sugar measurement is poor in operability, since a puncturing operation, a blood sampling operation and a measuring operation therein are carried out separately.

Furthermore, with the above-mentioned method, it may in some cases be difficult to efficiently obtain the blood.

DISCLOSURE OF INVENTION

It is a first object of the present invention to provide a component measuring instrument with which the measurement of a predetermined component of blood can be performed more securely and in a short time.

The first object as above can be attained by the present invention residing in the followings (1) to (15).

(1) A component measuring instrument used by mounting therein a chip having a puncture needle, including:

a specimen sampling portion application portion onto which a specimen sampling portion to be punctured is applied;

puncturing means for moving the puncture needle to puncture the specimen sampling portion applied onto the specimen sampling portion application portion;

pressure reducing means for putting the punctured portion of the specimen sampling portion punctured by the puncture needle, together with a containing space for the puncture needle, into a reduced-pressure condition;

measuring means for measuring the amount of a predetermined component in blood sampled from the punctured portion; and a chip retracting mechanism for moving the chip in a direction away from the specimen sampling portion while maintaining the reduced-pressure condition generated by the pressure reducing means.

(2) The component measuring instrument as set forth in paragraph (1) above, wherein the movement of the chip is carried out on the basis of the puncturing means in the condition where the chip is attached to the puncturing means.

(3) The component measuring instrument as set forth in paragraph (1) or (2) above, wherein the chip retracting mechanism is operated by utilizing a pressure reducing force generated by the operation of the pressure reducing means.

(4) The component measuring instrument as set forth in any of paragraphs (1) to (3) above, wherein the chip retracting mechanism includes a pressure reduction chamber, and at least one passage having a high air passage resistance for communication between the pressure reduction chamber and the containing space, and the pressure inside the pressure reduction chamber is reduced through the passage, thereby moving the chip in a direction away from the specimen sampling portion.

(5) The component measuring instrument as set forth in paragraph (1) or (2) above, wherein the chip retracting mechanism has a drive source for electric driving, and the chip retracting mechanism is operated by the driving of the drive source.

(6) The component measuring instrument as set forth in paragraph (5) above, wherein the drive source is a solenoid.

(7) The component measuring instrument as set forth in any of paragraphs (1) to (6), wherein the chip retracting mechanism has biasing means, and the chip is returned to its position before the operation of the chip retracting mechanism by the biasing means when the operation of the chip retracting mechanism is canceled.

(8) The component measuring instrument as set forth in any of paragraphs (1) to (7) above, wherein the component measuring instrument includes a housing for holding the chip and incorporating the puncturing means therein, and the pressure reducing means puts the containing space in the housing into a reduced-pressure condition.

(9) The component measuring instrument as set forth in any of paragraphs (1) to (8) above, wherein the operation of the puncturing means and the operation of the pressure reducing means can be started substantially simultaneously.

(10) The component measuring instrument as set forth in any of paragraphs (1) to (9) above, wherein the chip retracting mechanism is operated in succession to the operation of the pressure reducing means.

(11) The component measuring instrument as set forth in any of paragraphs (1) to (10) above, including moving distance determining means for determining the distance of movement of the chip by the chip retracting mechanism.

(12) The component measuring instrument as set forth in any of paragraphs (1) to (11) above, wherein the chip has a contact portion for making contact with the specimen sampling portion, and is used in such a manner that an opening provided on the inside of the contact portion is closed with the specimen sampling portion.

(13) The component measuring instrument as set forth in paragraph (12) above, wherein the specimen sampling portion application portion has a specimen sampling portion application surface, and the distal end of the contact portion is located at substantially the same position as the specimen sampling portion application surface or slightly projecting from the specimen sampling portion application surface, in the condition where the chip is mounted in the component measuring instrument.

(14) The component measuring instrument as set forth in any of paragraphs (1) to (13) above, wherein the chip comprises a test paper, and a blood passage for supplying blood to the test paper.

(15) The component measuring instrument as set forth in any of paragraphs (1) to (14) above, wherein the test paper is a test paper for blood sugar measurement.

In addition, it is a second object of the present invention to provide a chip with which a specimen can be securely sampled.

The second object as above can be attained by the present invention residing in the followings (16) to (27).

(16) A chip including:

a chip main body having a lumen portion; and an annularly projecting contact portion which is formed at the distal end of the chip main body and with which a specimen sampling portion is brought into contact, wherein at least a distal end portion of the contact portion decreases in thickness gradually along the direction from the proximal end toward the distal end thereof.

(17) The chip as set forth in paragraph (16) above, wherein the distal end of the contact portion is sharpened.

(18) The chip as set forth in paragraph (16) or (17), wherein the contact portion includes an inner wall surface on the inside thereof, and an outer wall surface on the outside thereof, and the inner wall surface and/or the outer wall surface is tapered, whereby the contact portion is varied in thickness.

(19) The chip as set forth in paragraph (18) above, wherein the angle between the inner wall surface and the outer wall surface in the vicinity of the distal end of the contact portion is 0.5 to 60°.

(20) The chip as set forth in any of paragraphs (16) to (19) above, wherein the chip main body has a flange at the outer circumference of a distal end portion thereof, and the distal end of the contact portion projects in the direction of the distal end from a distal end surface of the flange.

(21) The chip as set forth in any of paragraphs (16) to (20) above, wherein the height of the contact portion is 0.1 to 5 mm.

(22) The chip as set forth in any of paragraphs (16) to (21) above, wherein the contact portion is provided at its distal end with an opening so formed as to open the lumen portion, and the chip is used with the specimen sampling portion attracted under suction onto the opening by reducing the pressure inside the lumen portion, in the condition where the opening is closed with the specimen sampling portion.

(23) The chip as set forth in paragraph (22) above, wherein the aperture area of the opening is 10 to 50 mm$^2$.

(24) The chip as set forth in any of paragraphs (16) to (23) above, including a puncture needle which has a needle point passed through the lumen portion so as to puncture the specimen sampling portion.

(25) The chip as set forth in paragraph (24) above, wherein the needle point can be moved to a position in the vicinity of or beyond the distal end of the contact portion.

(26) The chip as set forth in any of paragraphs (16) to (25) above, including a test paper, and a specimen passage for supplying a specimen to the test paper.

(27) The chip as set forth in any of paragraphs (16) to (26) above, which is used in the state of being mounted in a component measuring instrument.

Furthermore, the present invention provides the following chip and component measuring instrument.

(28) The chip as set forth in paragraph (27) above, wherein the component measuring instrument is a component measuring instrument as set forth in any of paragraphs (1) to (15) above.

(29) The component measuring instrument as set forth in any of paragraphs (1) to (15) above, wherein the chip is a chip as set forth in any of paragraphs (16) to (26) above.

BEST MODE FOR CARRYING OUT THE INVENTION

Figure 1:
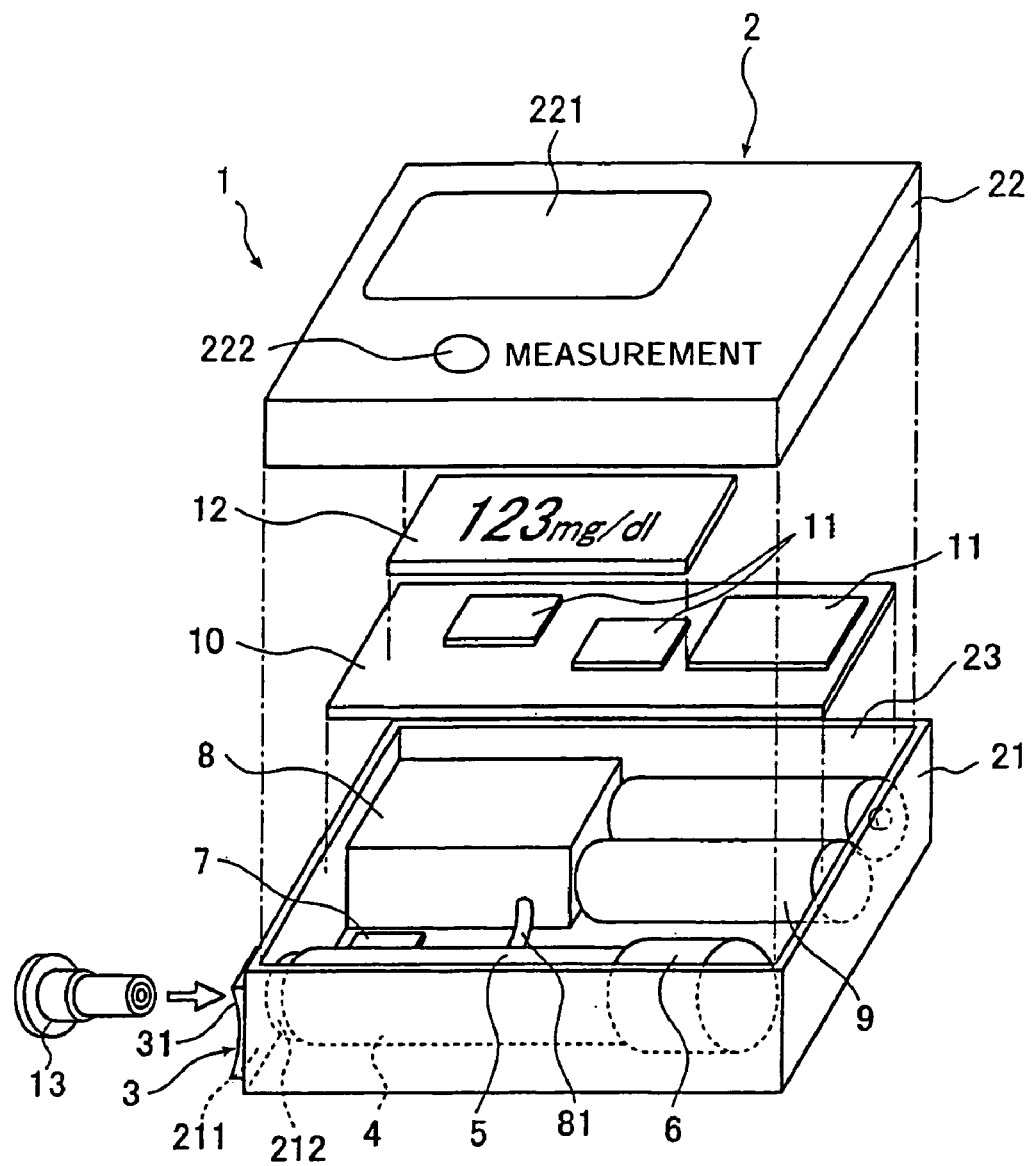
FIG. 1 is a perspective view showing the configuration of a first embodiment of the component measuring instrument according to the present invention.

In order to solve the above-mentioned problems, the present inventors have developed blood sugar measuring instruments in which a puncturing unit and a measuring unit are integrated with each other and which include a suction means for pressing a blood out, and has filed Japanese patent applications (Japanese Patent Application No. Hei 10-183794 (Japanese Patent Laid-open No. 2000-14662), and Japanese Patent Application No. Hei 10-330057 (Japanese Patent Laid-open No. 2000-152923)).

In using the blood sugar measuring instruments, first, a fingertip is applied onto the distal end of a chip, to seal the distal end opening of the chip so as to maintain gas-tightness. Next, the fingertip is punctured by a puncture needle projecting from the distal end opening, and, in this condition, the suction means is thereafter operated to attract the fingertip onto the distal end opening under suction and to suck out the blood from the punctured portion.

Furthermore, the present inventors have found out that when the suction means in such a blood sugar measuring instrument is operated to attract the fingertip onto the distal end of the chip under suction and then the fingertip and the chip in this condition are parted from each other, it is possible to suck out the blood from the punctured portion more securely, and to secure a necessary and sufficient amount of the blood in a short time. Based on the finding, the component measuring instrument according to the present invention has been completed.

On the other hand, for sampling a blood efficiently, it is necessary to bring the fingertip into close contact with the distal end opening more securely.

From such a point of view, the present inventors have found out that the property for close contact of the fingertip with the distal end opening is enhanced when the distal end of the chip is provided with a portion with which the fingertip is brought into contact and when the shape of the portion is appropriately selected. Based on the finding, the chip according to the present invention has been completed.

Now, the component measuring instrument and the chip according to the present invention will be described in detail below, based on preferred embodiments shown in the accompanying drawings.

The component measuring instrument according to the present invention is used in the condition where a chip comprising a puncture needle is mounted therein. The chip comprising a puncture needle to be used in the state of being mounted in the component measuring instrument according to the present invention is not particularly limited, but it is preferably a chip according to the present invention.

In addition, the use of the chip according to the present invention is not particularly limited. In a preferable mode, however, the chip of the present invention is used in the state of being mounted in a component measuring instrument, and, in a particularly preferable mode, the chip is used in the state of being mounted in a component measuring instrument according to the present invention.

Now, a mode in which a chip according to the present invention is mounted in a component measuring instrument according to the present invention will be described below, but the component measuring instrument of the present invention and the chip of the present invention are not limited to or by this mode.

First, the component measuring instrument according to the present invention will be described, and, particularly, the component measuring instrument for measuring the amount of glucose (predetermined component) in a blood specimen will be described as an example. In the present invention, the specimen sampling portion is not particularly limited. Preferable examples of the specimen sampling portion include a finger, an ear (for example, an earlobe), an abdominal portion, a thigh, an arm, etc. Here, the case where the specimen sampling portion is a finger (fingertip) will be described.

Figure 2:
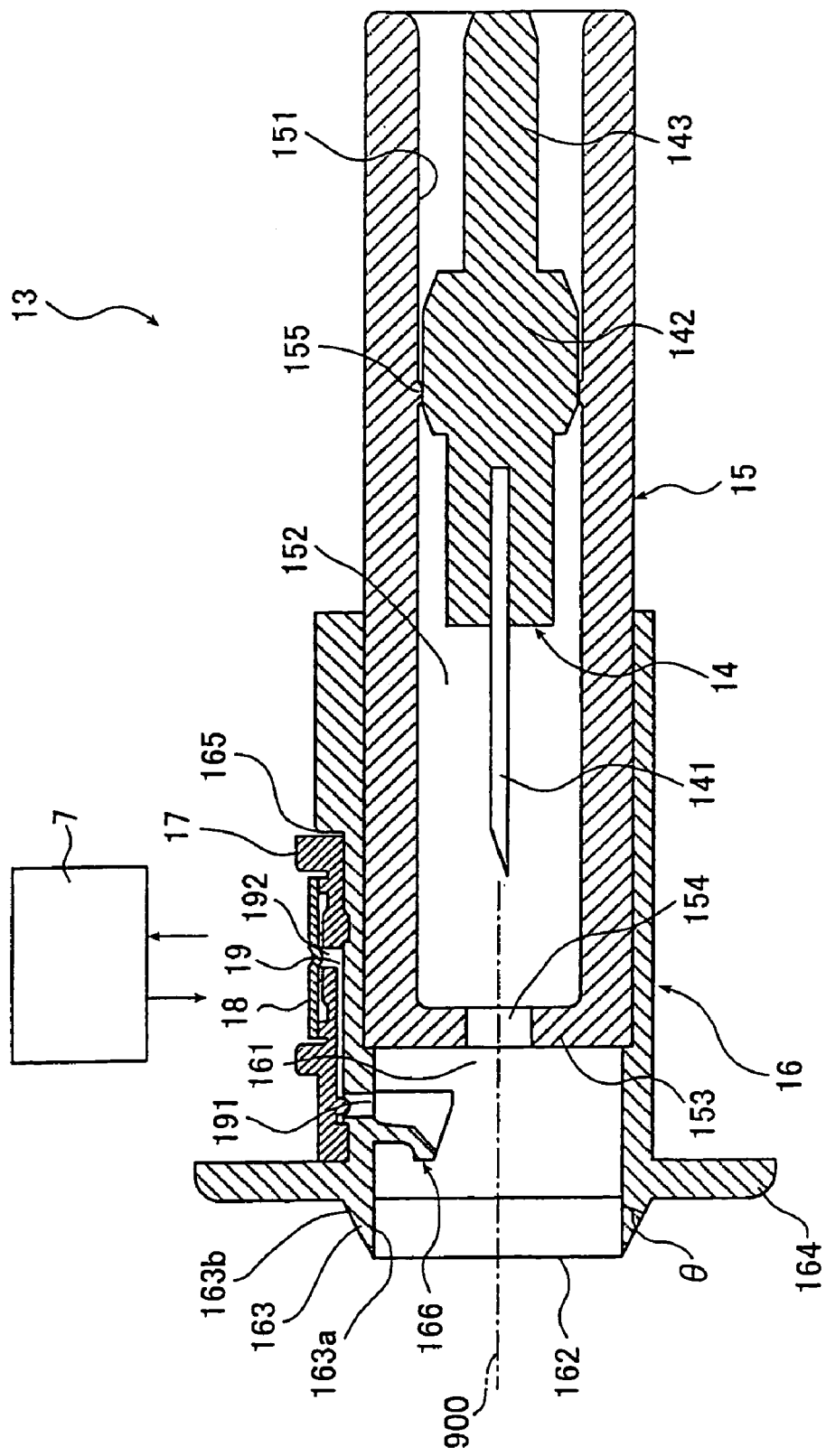
FIG. 2 is a vertical sectional view showing the configuration of a chip used in the present invention (a first embodiment of the chip according to the present invention).
Figure 3:
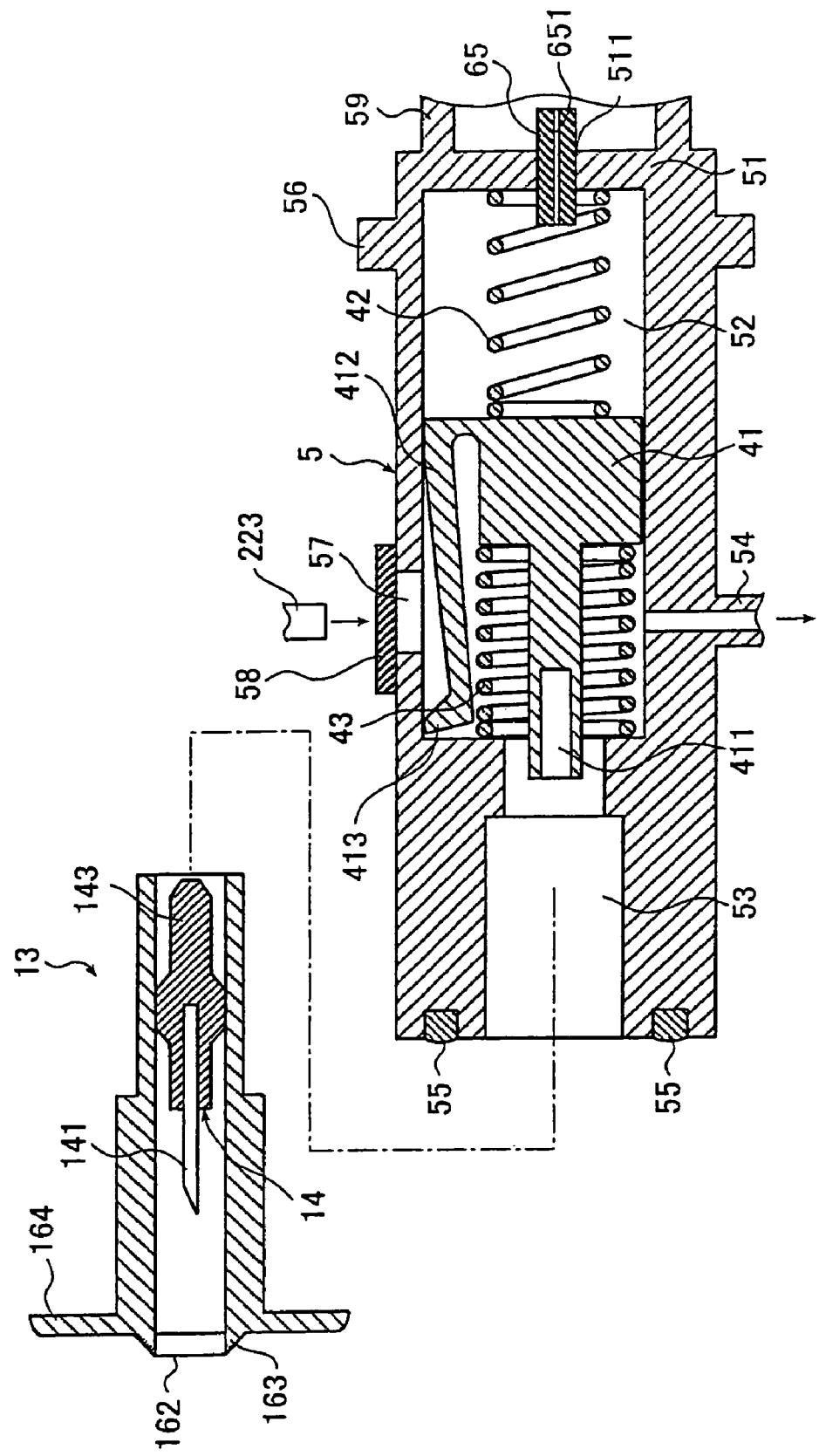
FIG. 3 is a vertical sectional view showing the configuration of a puncturing means and a housing incorporating the puncturing means therein provided in the first embodiment of the component measuring instrument (in the condition before mounting the chip in the housing).
Figure 4:
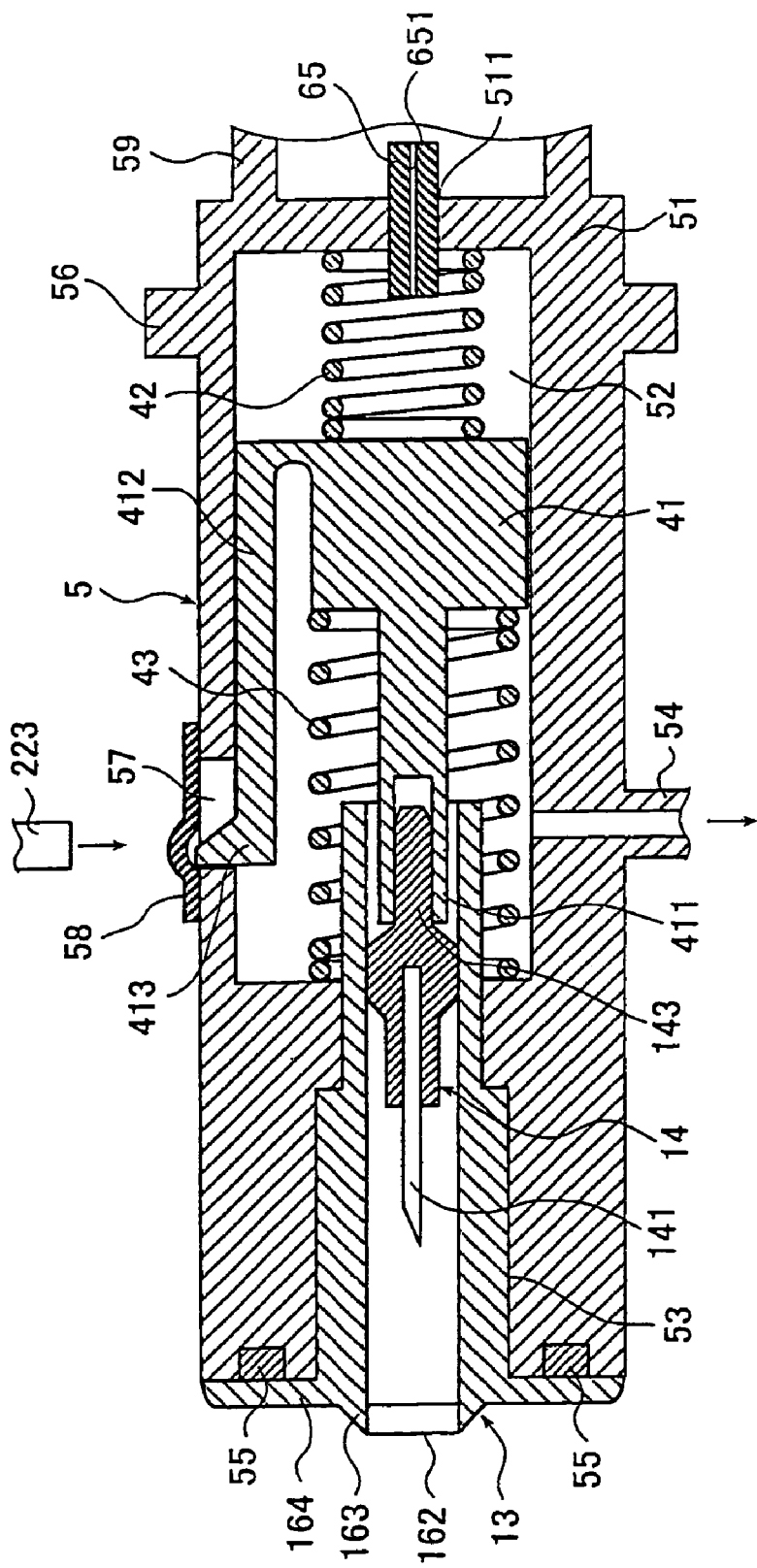
FIG. 4 is a vertical sectional view showing the configuration of the puncturing means and the housing incorporating the puncturing means therein provided in the first embodiment of the component measuring instrument (when the chip is mounted in the housing).

FIG. 1 is a perspective view showing schematically the configuration of a first embodiment of the component measuring instrument according to the present invention; FIG. 2 is a vertical sectional view showing the configuration of the chip used in the present invention; FIGS. 3 and 4 are vertical sectional views showing the configurations of a puncturing means and a housing incorporating the puncturing means therein which are provided in the first embodiment of the component measuring instrument; and FIGS. 5 to 8 are vertical sectional views showing a chip retracting mechanism provided in the first embodiment of the component measuring instrument. Incidentally, in FIGS. 1 to 8, the right side will be described as "the proximal end", and the left side as "the distal end".

As shown in FIG. 1, the component measuring instrument (blood component measuring instrument) 1 according to the first embodiment includes a main body 2, a finger application portion (specimen sampling portion application portion) 3 disposed in the main body 2, a puncturing means 4 contained in a housing 5, a chip retracting mechanism 6 provided on the proximal end side of the housing 5, a measuring means 7 for measuring a predetermined component in blood, a pump 8 for putting the inside of the housing 5 into a reduced-pressure condition, a battery 9, a control means 11 provided on a circuit board 10, and a display unit 12. The component measuring instrumental is used with a chip 13 mounted therein. Now, these constituent elements will be described.

The main body 2 is composed of a casing 21 and a cover 22 which face each other. The main body 2 is provided therein with a containing space 23, and the above-mentioned constituent elements 4 to 12 are contained in the containing space 23.

A wall portion 211 on the distal end side of the casing 21 is provided with an opening 212 which is circular in sectional shape and which pierces through the casing 21. The chip 13 is mounted (held) into the housing 5 which will be described later, through the opening 212.

In addition, a surface on the distal end side of the wall portion 211 is provided with a finger application portion 3 which surrounds the periphery of the opening 212 and which is formed in correspondence with the shape of a fingertip (finger). The finger application portion 3 is provided on the distal end side thereof with a finger application surface (specimen sampling portion application surface) 31. With a fingertip kept in contact with the finger application portion 3 (the finger application surface 31), the component measuring instrument 1 is operated. This results in that the fingertip is punctured, and the amount of a predetermined component (hereinafter represented by glucose) in the blood sampled is measured.

The top face of the cover 22 is provided with a display window (opening) 221 which pierces through the cover 22 and which is covered with a plate-like member formed of a transparent material.

The display unit 12 is disposed at a position inside the containing space 23 corresponding to the display window 221, and various kinds of information displayed on the display unit 12 can be confirmed through the display window 221.

The display unit 12 is comprised, for example, of a liquid crystal display device (LCD) or the like. For example, ON/OFF of a power source, a power source voltage (the residual power of the battery), a measurement, date and time of measurement, error indications, an operation guidance, and the like can be displayed on the display unit 12.

Besides, an operation button 222 is disposed at the top face of the cover 22. The component measuring instrument 1 is so constructed that pressing the operation button 222 causes the puncturing means 4 (described later) and the pump (pressure reducing means) 8 to be operated sequentially or substantially simultaneously.

Incidentally, the component measuring instrument 1 may be so constructed that pressing the operation button 222 causes a power source of the component measuring instrument 1 to be turned ON.

The circuit board 10 is disposed on the lower side in FIG. 1 of the display unit 12, and the control means 11 composed of a microcomputer is mounted on the circuit board 10. The control means 11 controls various operations of the component measuring instrument 1. In addition, the control means 11 incorporates an arithmetic unit for calculating the amount of glucose in the blood (blood sugar level) based on a signal from the measuring means 7.

The pump 8 as a pressure reducing means (suction means) is disposed on the left lower side in FIG. 1 of the circuit board 10. The pump 8 is operated by electric power, and is connected to an air duct 54 formed in the housing 5 which will be described later, through a tube 81. The tube 81 is flexible, and is formed of a polymeric material such as polyolefin, for example, polyvinyl chloride, polyethylene, polypropylene, ethylene-vinyl acetate copolymer (EVA) or the like, polyamide, polyester, silicone rubber, polyurethane, etc.

The pump 8 sucks and discharges air present in a lumen portion 52 of the housing 5, thereby putting the lumen portion 52 of the housing 5 into a reduced-pressure condition.

In addition, it suffices that the pump 8 can put the lumen portion 52 of the housing 5 and a punctured portion of the fingertip into a reduced-pressure condition to such a degree as to permit the blood to be sucked out from the punctured portion of the fingertip (for example, about 100 to 600 mmHg).

The battery 9 as a power source is disposed on the right lower side in FIG. 1 of the circuit board 10. The battery 9 is electrically connected to the pump 8, the control means 11, the display unit 12 and the like, for supplying electric power necessary for operations of these components.

The measuring means 7 is disposed on the viewer's side in FIG. 1 of the pump 8. The measuring means 7 is for optically measuring the amount of glucose in the blood developed on a test paper 18 provided in a chip 13 which will be described later. The installation position of the measuring means 7 is in the vicinity of a side portion where the test paper 18 is located in the condition where the chip 13 is mounted and held in the housing 5.

The measuring means 7 includes a light emitting device (light emitting diode) and a light receiving device (photodiode) which are not shown.

The light emitting device is electrically connected to the control means 11, and the light receiving device is electrically connected to the control means 11 through an amplifier and an A/D converter which are not shown.

The light emitting device is operated by a signal from the control means 11, thereby emitting light. The light is preferably a pulse of light which is intermittently emitted at a predetermined time interval.

When the light emitting device is turned ON in the condition where the chip 13 is mounted in the housing 5, the test paper 18 is irradiated with the light emitted from the light emitting device, and the reflected light from the test paper 18 is received by the light receiving device and is subjected to photo-electric conversion. The light receiving device outputs an analog signal according to the amount of light received, the analog signal is amplified in a desired manner, and is converted by the A/D converter into a digital signal, which is inputted to the control means 11.

The control means 11 performs a predetermined arithmetic processing based on the signal inputted, and, if required, performs a correction computation, to thereby determine the amount of glucose in the blood (blood sugar level). The blood sugar level thus determined is displayed on the display unit 12.

The housing 5 incorporating the puncturing means 4 therein and the chip retracting mechanism 6 provided in connection with the proximal end side of the housing 5 are disposed on the viewer's side in FIG. 1 of the measuring means 7.

The chip retracting mechanism 6 is attached to the casing 21. On the other hand, the housing 5 is not attached to the casing 21, and can be moved in the axial direction thereof (in the left-right direction in FIG. 1) by the chip retracting mechanism 6.

In the housing 5, the chip 13 is mounted for use. As shown in FIG. 2, the chip 13 includes a puncture needle 14, a first housing (needle housing) 15 for slidably containing the puncture needle 14 therein, a second housing (chip main body) 16 disposed at an outer circumferential portion of the first housing 15, a test paper fixing portion 17 disposed at an outer circumferential portion of the second housing 16, and a test paper 18 fixed to the test paper fixing portion 17.

The chip 13 to be mounted in the component measuring instrument according to the present invention is not particularly limited, but is preferably a chip according to the present invention which will be described later.

The puncture needle 14 is comprised of a needle body 141, and a hub 142 attached to the proximal end side of the needle body 141, and is contained in a lumen portion 152 of the first housing 15.

The needle body 141 is comprised of a hollow member or solid member formed of a metallic material, for example, stainless steel, aluminum, an aluminum alloy, titanium, a titanium alloy, or the like, and is provided at its distal end with a sharp knife edge (needle point). The surface (skin) of the fingertip is punctured by the knife edge.

Besides, the hub 142 is composed of a roughly cylindrical member, and is slid with an outer circumferential portion thereof in contact with the inner circumferential surface 151 of the first housing 15.

At a proximal end portion of the hub 142, a reduced-diameter portion 143 reduced in diameter is provided. The reduced-diameter portion 143 is fitted into a needle holder 411 of a plunger 41 constituting the puncturing means 4 which will be described later.

The first housing 15 is composed of a bottomed tubular member having a wall portion 153 as a bottom portion, and a lumen portion 152 is formed inside thereof.

The wall portion 153 is provided in a roughly central portion thereof with a hole 154 circular in sectional shape. The needle body 141 passes through the hole 154 at the time of puncturing a fingertip (finger). In addition, the diameter of the hole 154 is set to be smaller than the outside diameter of the distal end of the hub 142. Therefore, when the puncture needle 14 is moved in the direction of the distal end of the lumen portion 152 and the distal end of the hub 142 comes into contact with the proximal end of the wall portion 153, the puncture needle 14 is prevented from moving further in the direction of the distal end thereof. Therefore, the projecting length of the needle body 141 from the distal end of the chip 13 is kept constant at the time of puncturing the fingertip. Accordingly, the knife edge of the needle body 141 is securely prevented from puncturing the fingertip to a depth greater than a required depth.

In addition, a mechanism for regulating the moving distance of the plunger 41 which will be described later may be provided so as to regulate the puncturing depth of the knife edge of the needle body 141 into the fingertip.

The second housing 16 is attached to an outer circumferential portion of the first housing 15.

The second housing 16 is composed of a substantially tubular member, and a lumen portion 161 is formed inside thereof.

Besides, the second housing 16 is provided at the distal end thereof with a contact portion 163 projecting in a ring form. The contact portion 163 is a portion against which the fingertip is pressed, and a distal end opening (opening) 162 for opening the lumen portion 161 is formed inside thereof. The outer circumferential edge of the distal end of the contact portion 163 has a shape suitable for displaying an effect of mitigating the pain at the time of puncture by stimulating the surroundings of the punctured portion when it is pressed against the fingertip. In addition, it has such a shape that inflow of air through a gap between the distal end of the contact portion 163 and the surface of the fingertip is restrained as securely as possible when a reduced-pressure condition is generated by the pump 8. Incidentally, the distal end of the second housing 16 may not be provided with the contact portion 163 and, instead, the distal end surface of the second housing 16 may constitute a flat surface.

The second housing 16 is provided with a ring-formed flange 164 projecting outwards, at an outer circumferential portion in the vicinity of the proximal end of the contact portion 163. In the condition where the chip 13 is mounted in the housing 5 which will be described later, the flange 164 has its proximal end making contact with the distal end of the housing 5, thereby determining the position of the chip 13 relative to the housing 5.

The second housing 16 is provided with a recess 165 at an outer circumferential portion thereof, and a test paper fixing portion 17 with a disk form test paper 18 disposed thereon is mounted in the recess 165.

In addition, the second housing 16 is provided on its inner circumferential surface with a blood introducing guide 166 projecting into the lumen portion 161. The blood introducing guide 166 has the function of receiving the blood (specimen) flowing into the lumen portion 161 through the distal end opening 162 after the puncture of the fingertip.

In the chip 13 as above, a blood passage 19 is formed for communication between the lumen portion 161 of the second housing 16 and the exterior through the second housing 16 and the test paper fixing portion 17. The blood passage 19 is a conduit for guiding the blood obtained by the puncture to the test paper 18, and includes a passage opening 191 opened into the lumen portion 161 and a passage opening 192 opened to the exterior of the chip 13. Incidentally, the passage opening 192 is located at a central portion of the test paper 18.

In addition, the blood introducing guide 166 is provided in the vicinity of the passage opening 191. Therefore, the blood received by the blood introducing guide 166 is efficiently guided through the passage opening 191 into the blood passage 19. The blood reaches the passage opening 192 under capillarity, is supplied to the central portion of the test paper 18 disposed so as to close the passage opening 192, and is developed radially.

The test paper 18 comprises a carrier capable of absorbing and developing blood, and a reagent carried on the carrier.

Examples of the carrier include sheet form porous bodies such as a nonwoven fabric, a woven fabric, an oriented sheet, etc. Preferably, the porous body is hydrophilic.

The reagent to be carried on the carrier is determined as required, according to the component to be measured in the specimen. For example, in the case of use for measurement of blood sugar level, the reagent may include glucose oxidase (GOD), peroxidase (POD), and a color coupler (color coupling reagent) such as 4-aminoantipyrine, N-ethyl-N-(2-hydroxy-3-sulfopropyl)-m-toluidine, etc. Other than these substances, the reagent may include a substance capable of reacting with a blood component such as ascorbic acid oxidase, alcohol oxidase, cholesterol oxidase, etc., and a color coupler (color coupling reagent) the same with or similar to the above-mentioned. Besides, the reagent may further contain a buffer agent such as a phosphoric acid buffer solution. Incidentally, the kind and the components of the reagent are naturally not limited to the above-mentioned.

The chip 13 as above is detachably mounted (fitted) into the housing 5 (fitting portion 53) through the opening 212 of the casing 21 described above.

As shown in FIGS. 3 and 4, the housing 5 is composed of a bottomed tubular member having a wall portion 51 as a bottom portion, and a lumen portion (containing space) 52 is formed inside thereof. In addition, the housing 5 is provided on the distal end side thereof with the fitting portion 53 whose inside diameter is reduced correspondingly to the outer circumferential shape of the chip 13. The chip 13 is inserted and fitted (fixed) in the fitting portion 53. Incidentally, in FIGS. 3 and 4, the structure of the chip 13 is shown in a simplified form for easy understanding of the description.

The housing 5 is provided at its side portion with an air passage 54 for communication between the lumen portion 52 and the exterior, and the air passage 54 is connected to the pump 8 through a tube 81. Air inside the lumen portion 52 is sucked by the pump 8 through the air passage 54, whereby the lumen portion 52 is brought into a reduced-pressure condition.

The wall portion 51 is provided with a hole 511 in a roughly central portion thereof. A thin pipe 65 provided therein with an orifice (passage) 651 is disposed in the hole 511. Air is circulated between the lumen portion 52 and a variable-volume chamber 631 (described later), which are provided respectively on both sides of the thin pipe 65, through the orifice 651.

A ring form seal ring (sealing member) 55 is fitted to the distal end of the housing 55. This structure ensures that when the chip 13 is mounted in the housing 5, the proximal end of the flange 164 of the chip 13 makes contact with the seal ring 55, whereby gas-tightness of the lumen portion 52 is maintained.

The seal ring 55 is composed of an elastic material. Examples of the elastic material include various rubber materials such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, fluororubber, etc., and various thermoplastic elastomers such as styrene-based, polyolefin-based, polyvinyl chloride-based, polyurethane-based, polyester-based, polyamide-based, polybutadiene-based, and fluororubber-based thermoplastic elastomers, etc.

The housing 5 is provided at the outer circumference of a proximal portion thereof with a ring form flange 56 projecting outwards, and is provided at its proximal end with a cylindrical projection 59.

The puncturing means 4 is contained in the lumen portion 52, on the proximal end side of the fitting portion 53, of the housing 5. The puncturing means 4 has a structure in which the puncture needle 14 attached thereto is moved in the direction of the distal end, and a knife edge of the needle body 141 punctures the surface of a fingertip.

The puncturing means 4 includes a plunger 41, a coil spring (biasing member) 42 for biasing the plunger 41 in the direction of the distal end, and a coil spring (biasing member) 43 for biasing the plunger 41 in the direction of the proximal end.

The plunger 41 is provided with a cup-shaped needle holder 411 at a distal end portion thereof. The reduced-diameter portion 143 of the puncture needle 14 is detachably fitted in the needle holder 411. In addition, the plunger 41 is provided at its proximal end portion with an elastically deformable elastic piece 412 having a projection-like engaging and stopping portion 413 at its distal end.

In the condition before the chip 13 is mounted in the housing 5, i.e., in the condition (see FIG. 3) before the puncture needle 14 is attached to the plunger 41, the engaging and stopping portion 413 is biased upwards in FIG. 3 by an elastic force of the elastic piece 412 so as to make contact with the inner circumferential surface of the housing 5. On the other hand, in the condition where the chip 13 is mounted in the housing 5, i.e., in the condition (see FIG. 4) where the puncture needle 14 is attached to the plunger 41, the engaging and stopping portion 413 is inserted in an opening 57 piercing through the housing 5 and is engaged and stopped at an edge portion of the opening 57. This results in that the plunger 41 is restrained from moving in the direction of the distal end. Incidentally, the opening 57 is closed with a flat plate form seal member (sealing member) 58, whereby the gas-tightness of the lumen portion 52 is maintained. The seal member 58 can be formed of the same material as that of the above-mentioned seal ring 55.

The coil spring (puncture spring) 42 is disposed on the proximal end side of the plunger 41, and both ends thereof are in contact with the plunger 41 and the wall portion 51, respectively. On the other hand, the coil spring (push-back spring) 43 is disposed on the distal end side of the plunger 41, and both ends thereof are in contact with the plunger 41 and the fitting portion 53, respectively.

In addition, as shown in FIGS. 3 and 4, an engaging-and-stopping cancel member 223 capable of moving the engaging and stopping portion 413 into the lumen portion 52 (in the direction of arrow in the figures) is provided in the exterior of the housing 5. The engaging-and-stopping cancel member 223 is moved in conjunction with the pressing on the operation button 222 described above.

In the condition where the engaging and stopping portion 413 is engaged and stopped with the opening 57, the coil spring 42 is in a compressed state and biases the plunger 41 in the direction of the distal end. When the operation button 222 is pressed to move the engaging-and-stopping cancel member 223 in the direction of arrow in the figures with the result of cancellation of the engaged and stopped state of the engaging and stopping portion 413, the coil spring 42 extends to move the plunger 41 in the direction of the distal end, thereby causing the knife edge of the needle body 141 to puncture the surface (skin) of the fingertip.

In this instance, on the other hand, the coil spring 43 is compressed and biases the plunger 41 in the direction of the proximal end, i.e., it tends to push back the plunger 41 in the direction of the proximal end. Thereafter, the plunger 41 performs an attenuating motion, and eventually stands still at a position where the elastic force of the coil spring 42 and the elastic force of the coil spring 43 balance with each other.

Incidentally, in the condition where the plunger 41 stands still, the knife edge of the needle body 141 is contained in the chip 13.

The chip retracting mechanism 6 is provided on the proximal end side of the housing 5.

The chip retracting mechanism 6 is for moving the housing 5 and the chip 13, which is mounted in the housing 5, in the direction away from the fingertip 20 (in the direction of the proximal end).

As shown in FIGS. 5 to 8, the chip retracting mechanism 6 includes a main body portion 61, a seal ring 64, and the thin pipe 65.

The main body portion 61 is composed of a bottomed tubular member having a wall portion 62 as a bottom portion, and a lumen portion 63 is formed inside thereof. The proximal end side of the housing 5 is inserted in the lumen portion 63.

The main body portion 61 is provided at its distal end with a ring form projection 611 projecting toward the center thereof. In the condition before the operation of the chip retracting mechanism 6, the proximal end of the projection 611 and the distal end of the flange 56 are in contact with each other. This restrains the housing 5 from moving in the direction of the distal end. Namely, this can prevent the housing 5 from slipping off from the main body portion 61.

Figure 5:
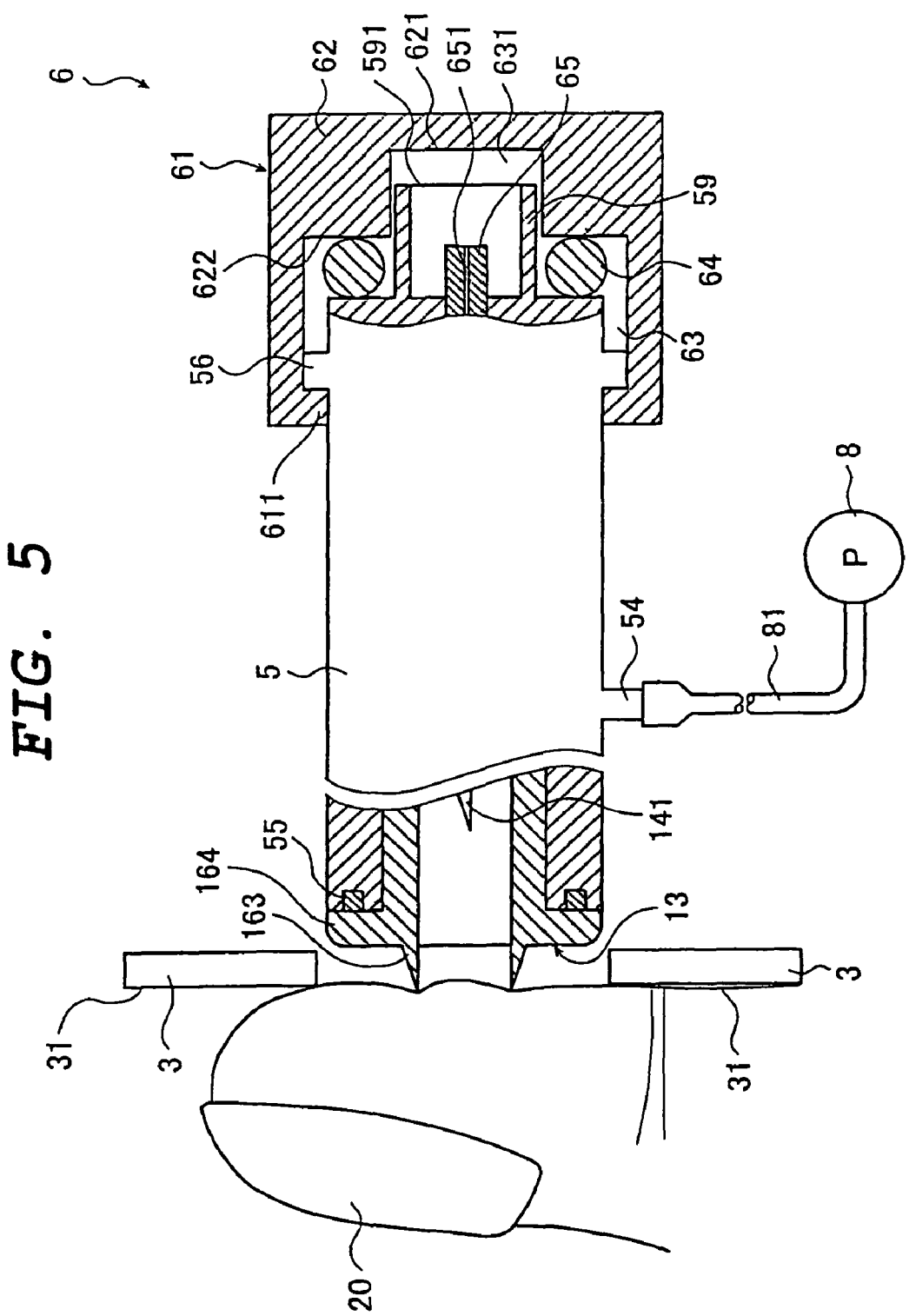
FIG. 5 is a vertical sectional view showing the configuration of a chip retracting mechanism provided in the first embodiment of the component measuring instrument (before the operation of the puncturing means).

Besides, in this instance, the distal end of the contact portion 163 is located at roughly the same position as the finger application surface 31 or is projecting slightly from the finger application surface 31 (see FIG. 5). This ensures that when the fingertip 20 makes contact with the finger application portion 3, the surface of the fingertip 20 securely makes contact with the contact portion 163, whereby the distal end opening 162 can be closed.

The wall portion 62 is provided in a roughly central portion thereof with a recess 621 circular in sectional shape. The diameter of the recess 621 is set to be substantially equal to the outside diameter of the projection 59, and the projection 59 is inserted in the recess 621. In addition, the outside diameter of the flange 56 is set to be substantially equal to the inside diameter of the main body portion 61. This configuration makes it possible to securely prevent, for example, an offset in the vertical direction in the figures (an offset between the centers of the housing 5 and the main body portion 61), irrespectively of the position in the axial direction of the housing 5.

A ring form seal ring 64 is disposed between the outer circumference of the projection 59, namely, the proximal end of the housing 5 and a distal end side surface 622 of the wall portion 62. The seal ring 64 is in gas-tight close contact with both the proximal end of the housing 5 and the surface 622.

This results in that a gas-tight variable-volume chamber (pressure reduction chamber) 631 is defined in a region surrounded by the seal ring 64, the proximal end of the housing 5, the surface 622, and the inside surfaces of the recess 621.

In addition, the seal ring 64 is composed of an elastic material, and, in an operating condition of the chip retracting mechanism 6 (in the condition shown in FIG. 8), the seal ring 64 by its elastic force biases the housing 5 in the direction of the distal end. Namely, the seal ring 64 functions also as a biasing means. As such an elastic material, the same material as that of the above-described seal ring 55 and the like can be used.

The thin pipe 65 is composed of a cylindrical member, and the orifice (passage) 651 is formed inside thereof. The orifice 651 is a passage for communication between the lumen portion 52 of the housing 5 and the variable-volume chamber 631, and has a high air passage resistance due to the small diameter thereof. The diameter of the orifice 651 is not particularly limited; for example, the diameter is preferably about 0.01 to 0.3 mm. With the diameter of the orifice 651 set within this range, it is possible to obtain a necessary and sufficient air passage (circulation) resistance.

Besides, by regulating the diameter of the orifice 651, it is possible to regulate the starting timings of the operation of the pump 8 and the operation of the chip retracting mechanism 6.

Incidentally, the thin pipe 65 is not limited to the one shown in the figures, and, if required, a plurality of the thin pipes 65 may be disposed.

In the chip retracting mechanism 6 as above, when the fingertip 20 is brought into contact with the contact portion 163 to seal the distal end opening 162 and the pump 8 is operated under this condition, first, the lumen portion 52 is brought into a reduced-pressure condition, so that air present inside the variable-volume chamber 631 flows through the orifice 651 into the lumen portion 52, whereby pressure reduction in the variable-volume chamber 631 is started. Since the orifice 651 has a high air passage resistance, the volume of the variable-volume chamber 631 is gradually decreased, and the housing 5 and the chip 13 mounted therein are gradually moved in the direction away from the fingertip 20.

Figure 8:
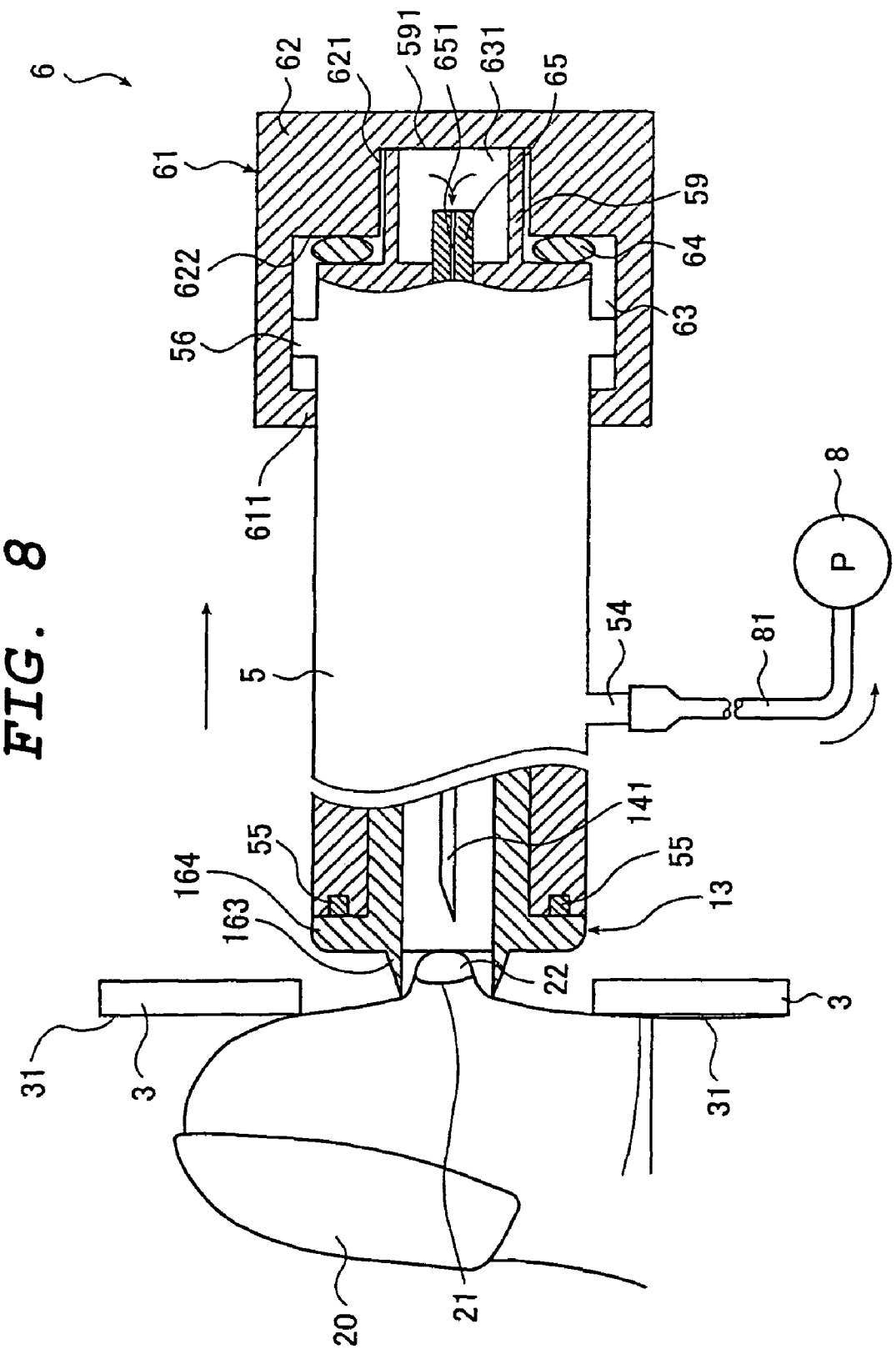
FIG. 8 is a vertical sectional view showing the configuration of the chip retracting mechanism provided in the first embodiment of the component measuring instrument (when the chip retracting mechanism is operated).

Before long, the proximal end 591 of the projection 59 comes into contact with the bottom surface of the recess 621, whereupon the movement of the housing 5 and the chip 13 mounted therein in the direction of the proximal end is stopped (see FIG. 8). Therefore, by regulating the axial length of the projection 59, it is possible to prevent the chip 13 from being spaced away from the fingertip 20 more than required. In other words, the projection 59 and the bottom surface of the recess 621 coming into contact therewith constitute a means (moving distance determining means) for determining the moving distance (maximum retraction distance) of the chip 13 from the fingertip 20.

The away distance between the chip 13 and the fingertip 20 (the maximum retraction distance of the chip 13) as above is not particularly limited; for example, the away distance is preferably about 0.2 to 2.5 mm, and more preferably about 0.5 to 1.5 mm. With the away distance set in this range, it is possible to obtain a sufficient amount of blood more securely and in a short time. Besides, it is possible to securely prevent the fingertip 20 from slipping off from the distal end opening 162.

In addition, the chip retracting mechanism 6 operates in succession to the operation of the pump 8. Specifically, the chip retracting mechanism 6 is so designed as to gradually retract (move) the chip 13 in the direction of the proximal end after the fingertip 20 is attracted under suction onto the distal end opening 162 by reducing the pressure inside the lumen portion 52 by the pump 8. Therefore, the chip retracting mechanism 6 can bring the chip 13 away from the fingertip 20 while maintaining the punctured portion 21 of the fingertip 20 in a reduced-pressure condition.

The chip retracting mechanism 6 as above-described operates by utilizing the pressure reducing power generated by the pump 8. In other words, the pump (pressure reducing means) 8 may be said to be one of the constituent elements of the chip retracting mechanism 6.

In addition, the chip retracting mechanism 6 as above-described does not need an addition of other drive source, and, therefore, it is advantageous for reductions in the size, weight, and manufacturing cost of the component measuring instrument 1.

Figure 6:
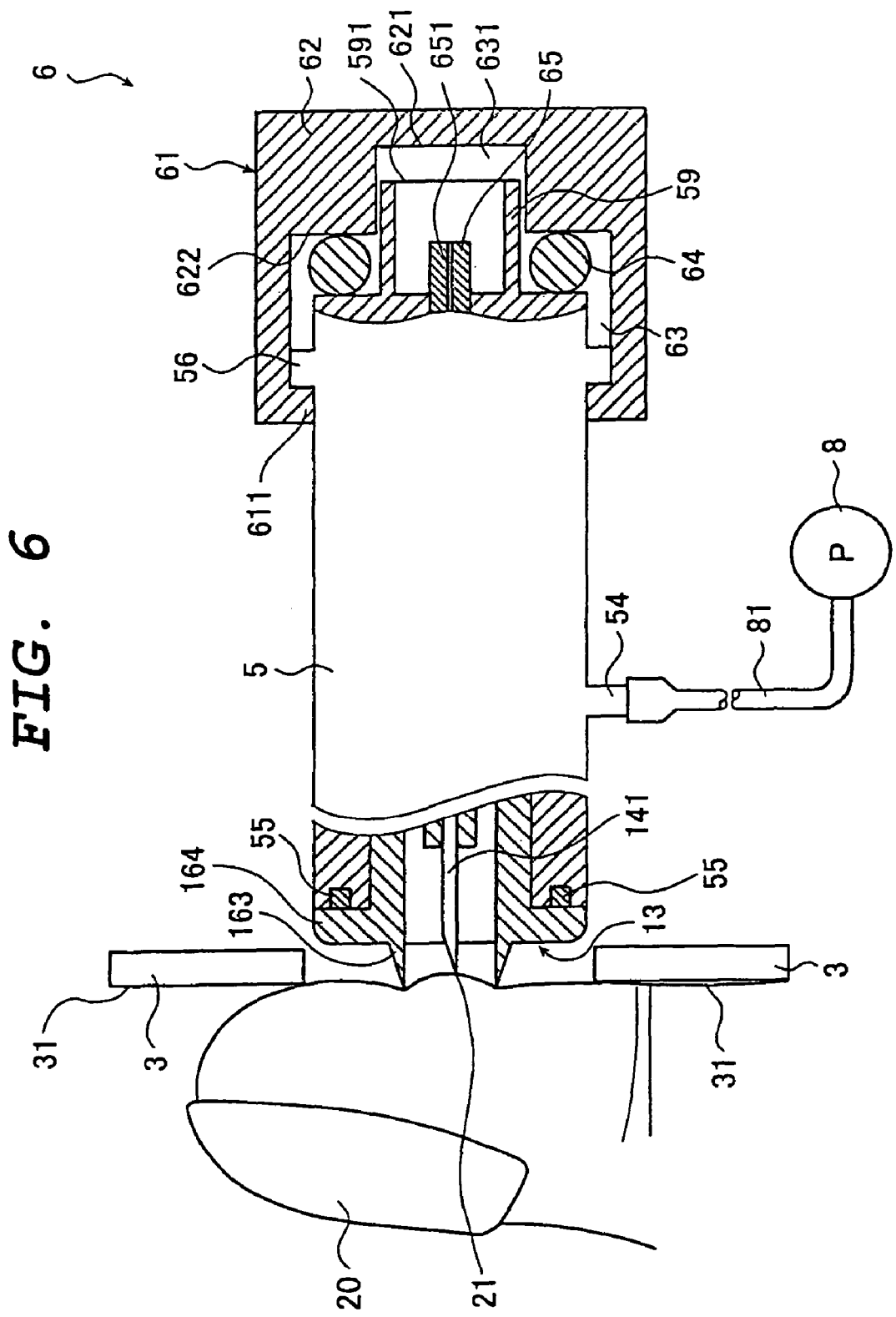
FIG. 6 is a vertical sectional view showing the configuration of the chip retracting mechanism provided in the first embodiment of the component measuring instrument (when the puncturing means is operated).
Figure 7:
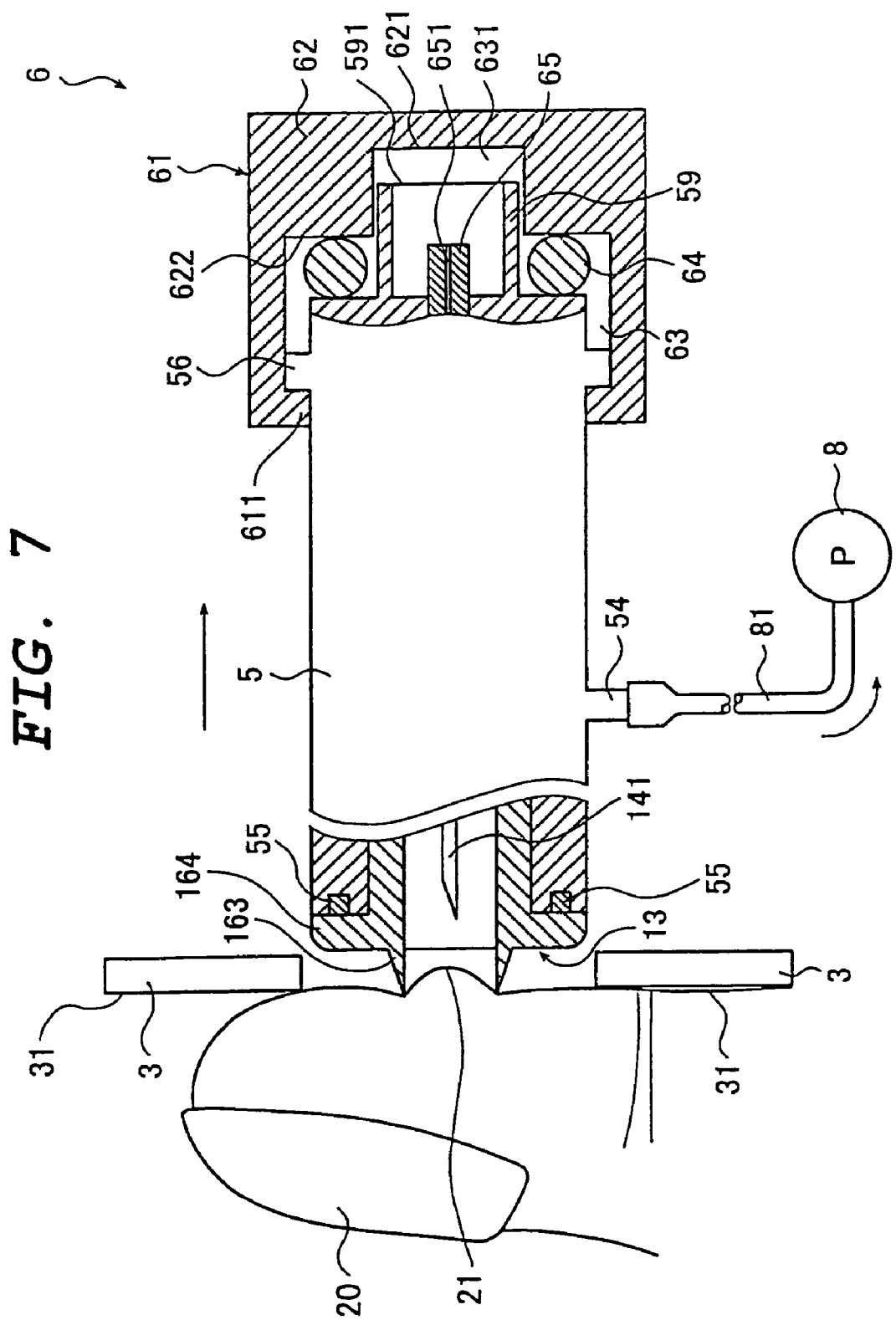
FIG. 7 is a vertical sectional view showing the configuration of the chip retracting mechanism provided in the first embodiment of the component measuring instrument (when the pressure reducing means is operated).

Incidentally, in the component measuring instrument 1, when the fingertip 20 is pressed against the finger application portion 3 as shown in FIG. 6, the surface of the fingertip 20 makes contact with the distal end of the contact portion 163, and the distal end of the contact portion 163 applies a pressure to capillary vessels in the surroundings of the punctured portion 21.

Therefore, in the case of a component measuring instrument 1 not provided with the chip retracting mechanism 8, even when the pump 8 is operated to bring the punctured portion 21 into a reduced-pressure condition for the purpose of sucking the blood out from the punctured portion 21, it is impossible to obtain a blood amount necessary for measurement of glucose level or it takes a long time to obtain a sufficient amount of blood, since the pressure applied to the capillary vessels in the surroundings of the punctured portion 21 has not yet been cancelled.

On the contrary, in the component measuring instrument 1 according to the present invention, the chip 13 can be moved away from the fingertip 20 while maintaining the punctured portion 21 of the fingertip 20 in the reduced-pressure condition, so that the capillary vessels in the surroundings of the punctured portion 21 having been pressed by the distal end of the contact portion 163 are released from the pressure, the blood 22 is sucked out from the punctured portion 21 more securely and in a short time, and a necessary and sufficient amount of blood for measurement of glucose level can be obtained assuredly.

In addition, in the operating condition of the chip retracting mechanism 6 (the condition shown in FIG. 8), the housing 5 is moved in the direction of the proximal end, and the seal ring 64 is put into a compressed state. Since the seal ring 64 is composed of an elastic material as above-described, it is biasing the housing 5 in the direction of the distal end in the condition shown in FIG. 8. When the reduced-pressure condition by the pump 8 is canceled by a pressure reduction canceling means (not shown), therefore, the seal ring 64 returns substantially to its original shape under its own elastic force, thereby moving the housing 5 in the direction of the distal end. In this case, the distal end of the flange 56 of the housing 5 comes into contact with the proximal end of the projection 611 of the main body portion 61, and is thereby restrained from moving further in the direction of the distal end. Namely, the housing 5 and the chip 13 mounted therein are returned to the positions where they have been before the operation of the chip retracting mechanism 6.

Now, the operations of the components of the component measuring instrument 1 in the case of performing puncture, sampling and development of blood, and measurement of blood sugar level by use of the component measuring instrument 1 will be described below, referring to FIGS. 2 to 8.

[1] First, the chip 13 is inserted into the fitting portion 53 of the housing 5 through the opening 212 of the casing 21, and the reduced-diameter portion 143 of the puncture needle 14 is fitted into the needle holder 411 (see FIGS. 3 and 4).

When the chip 13 is pushed in further in the direction of the proximal end, the plunger 41 is moved in the direction of the proximal end against the biasing force of the coil spring 42. The engaging and stopping portion 413 is in contact with the inner circumferential surface of the lumen portion 52 under the biasing by the elastic force of the elastic piece 412, but, when the engaging and stopping portion 413 comes to the position of the opening 57, it is inserted into the opening 57 (see FIG. 4). This results in that, even when the pushing force in the direction of the proximal end by the chip 13 is canceled, the engaging and stopping portion 413 is engaged and stopped with the opening 57, whereby the plunger 41 is restrained from moving in the direction of the distal end. In this instance, the coil spring 42 is in a compressed state. In this condition, preparation for puncture by the puncture needle 4 and preparation for blood (specimen) sampling have been completed.

[2] Next, a power source switch which is not shown is turned ON. This results in that the components of the component measuring instrument 1 are started, and a condition where measurement is possible is attained.

[3] Subsequently, a fingertip (finger) 20 is pressed against the finger application portion 3. As a result, the fingertip 20 is brought into pressure contact with the contact portion 163 of the chip 13. In this case, the fingertip 20 is so set as to close the distal end opening 162 therewith (see FIG. 5) for minimizing the leakage of air.

[4] When the operation button 222 is pressed, the engaging-and-stopping cancel member 223 in connection with the operation button 222 is moved to the lower side in FIG. 4. This results in that the engaging-and-stopping cancel member 223 makes contact with the engaging and stopping portion 413, and pushes back the engaging and stopping portion 413 to the side of the lumen portion 52. By this operation, the engaging and stopping of the engaging and stopping portion 413 is canceled, and the elastic force of the coil spring 42 having been compressed moves the plunger 41 in the direction of the distal end, whereby the needle body 141 is projected through the distal end opening 162, to puncture the surface of the fingertip 20 (see FIG. 6). The punctured portion 21 punctured by the needle body 141 bleeds.

Incidentally, with the operation button 222 pressed, an operation switch (not shown) for the pump 8 is turned ON substantially simultaneously.

[5] After the fingertip 20 is punctured by the needle body 141, the coil spring 43 pushes back the plunger 41 in the direction of the proximal end. The plunger 41 undergoes an attenuation motion, to stand still at a position where the elastic force of the coil spring 42 and the elastic force of the coil spring 43 balance with each other (see FIG. 7). In this instance, the knife edge of the needle body 141 is contained in the chip 13. Thus, the knife edge of the needle body 141 is prevented from projecting from the distal end opening 162 at other times than the time of puncturing. Therefore, mistaken damaging of the skin or the like is obviated, and infection can be prevented, with the result of high safety.

[6] Substantially simultaneously with the operation of [4] above, the pump 8 is operated, to start suction of air out of the lumen portion 52 of the housing 5. This lowers the pressure inside the lumen portion 52, resulting in a reduced-pressure condition.

In this instance, the punctured portion 21 punctured by the needle body 141 of the fingertip 20 is also in a reduced-pressure condition. It should be noted here that in this condition, the fingertip 20 located inside of the contact portion 163 (or at the distal end opening 162) rises in a hill form toward the inside of the chip 13, and capillary vessels are under pressure in the surroundings of the punctured portion 21 with which the distal end of the contact portion 163 is in contact.

[7] When the suction of air out of the lumen portion 52 by the pump 8 is continued further, air inside the variable-volume chamber 631 gradually flows out through the orifice 651 into the lumen portion 52, and the volume of the variable-volume chamber 631 decreases gradually. As a result, the housing 5 and the chip 13 mounted thereon start gradually moving in the direction of the proximal end, namely, in the direction away from the fingertip 20.

In this instance, the reduced-pressure condition in the lumen portion 52 and at the punctured portion 21 of the fingertip 20 is maintained, so that the fingertip 20 is prevented from slipping off from the distal end opening 162. In addition, even though the chip 13 is moved away from the fingertip 20, the fingertip 20 does not move following up to the chip 13 because it is in contact with the finger application portion 3. Therefore, the chip 13 is securely moving away from the fingertip 20.

With the chip 13 moving away from the fingertip 20, the capillary vessels in the surroundings of the punctured portion 21 which have been receiving the pressure applied by the distal end of the contact portion 163 are released gradually, and the blood 22 is sucked out from the punctured portion 21 (see FIG. 8). Namely, as compared to the case where the moving away of the fingertip 20 and the chip 13 from each other is not adopted, the bleeding is promoted in this case, so that it is possible to secure a necessary amount of blood in a short time.

Incidentally, the minimum pressure produced by the pump 8 is preferably about 100 to 600 mmHg, for example.

Before long, the proximal end 591 of the projection 59 and the bottom surface of the recess 621 come into contact with each other. This stops the movement of the housing 5 and the chip 13 mounted therein in the direction of the proximal end. Thus, the chip 13 is stopped at a position spaced by an appropriate distance from the fingertip 20, so that the fingertip 20 is prevented from slipping off from the distal end opening 162. Therefore, the trouble that the blood 22 sucked out from the punctured portion 21 would scatter to contaminate the surroundings can be prevented more assuredly, with the result of high safety.

As described above, in the component measuring instrument 1, the single pressing of the operation button 222 causes the puncturing operation and the pressure reducing operation to be performed substantially simultaneously, and the retracting operation of the chip 13 is effected by utilizing the pressure reducing power provided by the pump 8. Therefore, the component measuring instrument 1 is extremely excellent in operability.

[8] Next, the blood 22 raised in a grain form on the punctured portion 21 by the operation of [7] above makes contact with the blood introducing guide 166 formed inside of the chip 13, is guided through the blood passage 19 to the test paper 18, is supplied to a central portion of the test paper 18, and is developed radially (see FIG. 2).

Attendant on the supply and development of the blood 22 onto the test paper 18, glucose (the component to be measured) in the blood 22 and the reagent carried on the test paper 18 react with each other, resulting in coloration of the test paper 18 according to the glucose level. The degree of the coloration is measured by the above-described measuring means 7, an arithmetic operation is carried out by the control means 11 based on the data thus obtained, and corrections such as temperature correction and hematocrit value correction are performed, to quantify the blood sugar level. Then, the result is displayed on the display unit 12.

[9] After confirmation of the measurement result, a pressure reduction canceling means (not shown) is operated, whereupon the outside air flows into the lumen portion 52 and to the punctured portion 21, to bring the lumen portion 52 and the punctured portion 21 back to the atmospheric pressure. When it is confirmed that the suction feeling in the surroundings of the punctured portion 21 of the fingertip 20 has been removed and that the punctured portion 21 has been returned to the atmospheric pressure, the contact portion 163 of the chip 13 is parted from the fingertip 20. Incidentally, examples of the pressure reduction canceling means include a release valve or the like (not shown) provided at an intermediate portion of the tube 81.

Next, a second embodiment of the component measuring instrument according to the present invention will be described.

The second embodiment of the component measuring instrument differs from the first embodiment in the configuration of the chip retracting mechanism.

Figure 9:
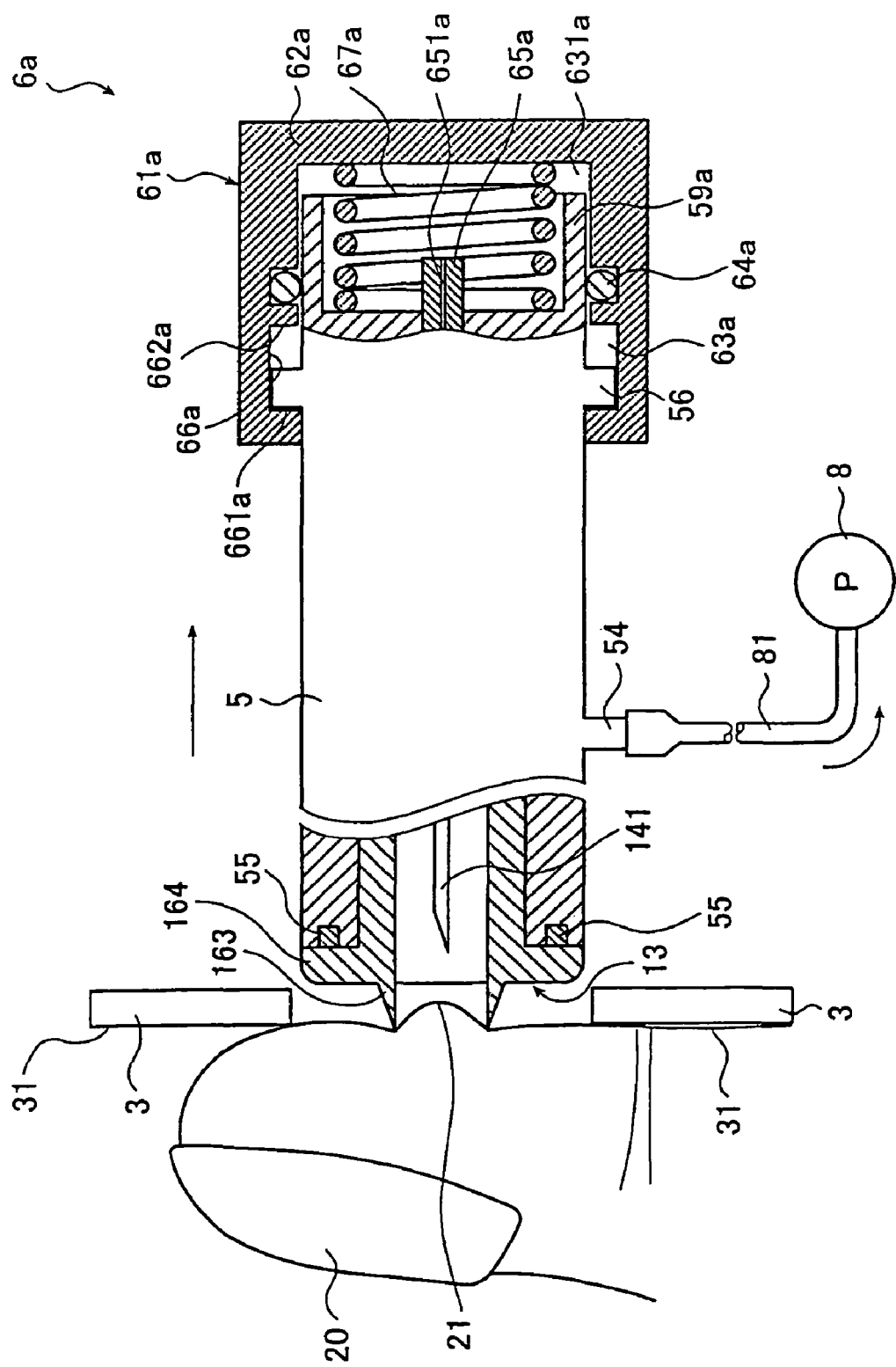
FIG. 9 is a vertical sectional view showing the configuration of the chip retracting mechanism provided in a second embodiment of the component measuring instrument (when the pressure reducing means is operated).

FIG. 9 is a sectional view showing the configuration of a chip retracting mechanism provided in the second embodiment of the component measuring instrument.

Now, description of the chip retracting mechanism 6a shown in FIG. 9 will be made centering on the difference thereof from the first embodiment, and description of the same items as those in the first embodiment will be omitted. In the following description, the right side in FIG. 9 will be referred to as "the proximal end", and the left side as "the distal end".

The chip retracting mechanism 6a includes a main body portion 61a, a seal ring 64a, a thin pipe 65a, and a coil spring 67a.

The main body portion 61a is composed of a bottomed tubular member having a wall portion 62a as a bottom portion, and a lumen portion 63a is formed inside thereof. The proximal end side of a housing 5 is inserted in the lumen portion 63a.

The main body portion 61a is provided with a ring form recess 66a at the inner circumference of a distal end portion thereof, and a flange 56 of the housing 5 is located in the recess 66a. In addition, the recess 66a comprises a distal end side inner surface 661a at the distal end thereof, and a proximal end side inner surface 662a at the proximal end thereof. The distal end side inner surface 661a and the proximal end side inner surface 662a together restrict the flange 56 from moving in the axial direction. Namely, the movement of the housing 5 in the axial direction is restricted by the distal end side inner surface 661a and the proximal end side inner surface 662a.

In the operating condition of the chip retracting mechanism 6a, the proximal end of the flange 56 and the proximal end side inner surface 662a make contact with each other, whereby the movement of the housing 5 and a chip 13 mounted therein in the direction of the proximal end is restricted. In other words, the flange 56 and the proximal end side inner surface 662a in contact therewith constitute a means (moving distance determining means) for determining the moving distance (maximum retraction distance) of the chip 13 from a fingertip 20.

The ring form seal ring 64a is fitted in the vicinity of a central portion of the inner circumferential surface of the main body portion 61a, and is so disposed as to make gas-tight close contact with the outer circumferential surface of the housing 5 and the outer circumferential surface of a ring form projection 59a formed at the proximal end of the housing 5. As a result, a gas-tight variable-volume chamber (pressure reduction chamber) 631a is defined in a region surrounded by the seal ring 64a, the proximal end of the housing 5, and the inside surfaces of the lumen portion 63a, whereby the gas-tightness of the variable-volume chamber 631a is maintained irrespectively of the position in the axial direction of the housing 5. In this case, the seal ring 64a preferably has a sliding resistance on such a level as not to hinder the extension and contraction of a coil spring 67a which will be described later.

The seal ring 64a as above can be formed of the same material as that of the above-mentioned seal ring 55 and the like.

In addition, the coil spring 67a is disposed as a biasing means in the variable-volume chamber 631a, the proximal end of the coil spring 67a is in contact with the wall portion 62a, and the distal end of the coil spring 67a is in contact with the proximal end of the housing 5. In the operating condition of the chip retracting mechanism 6a, the housing 5 is moved in the direction of the proximal end, and the coil spring 67a is in a compressed state, thereby biasing the housing 5 in the direction of the distal end.

With this configuration, also, the same functions and effects as those in the chip retracting mechanism in the first embodiment above can be obtained.

Next, a third embodiment of the component measuring instrument according to the present invention will be described.

The third embodiment of the component measuring instrument differs from the above embodiments in the configuration of the chip retracting mechanism.

Figure 10:
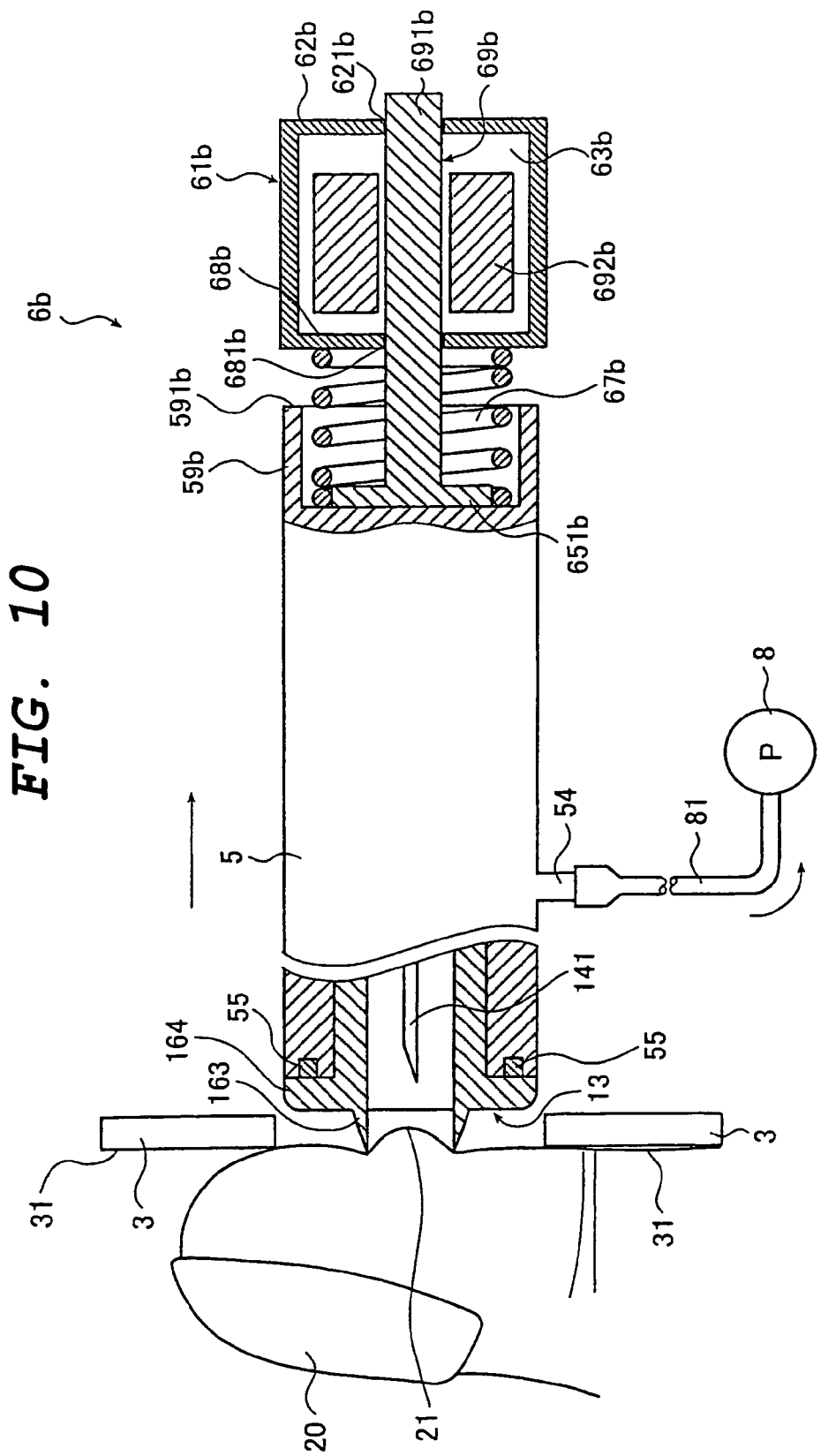
FIG. 10 is a vertical sectional view showing the configuration of the chip retracting mechanism provided in a third embodiment of the component measuring instrument (when the pressure reducing means is operated).

FIG. 10 is a sectional view showing the configuration of a chip retracting mechanism provided in the third embodiment of the component measuring instrument.

Now, description of the chip retracting mechanism 6b shown in FIG. 10 will be made centering on the difference thereof from the first and second embodiments above, and description of the same items as those in the above embodiments will be omitted. In the following description, the right side in FIG. 10 will be referred to as "the proximal end", and the left side as "the distal end".

The chip retracting mechanism 6b includes a main body portion 61b, a solenoid 69b, and a coil spring 67b.

The main body portion 61b is composed of a bottomed tubular member having a wall portion 62b as a bottom portion, and a lumen portion 63b is formed inside thereof. In addition, the main body portion 61b is provided with a wall portion 68b at the distal end thereof.

The wall portions 62b and 68b are provided respectively with holes 621b and 681b in roughly central portions thereof, and a plunger 691b having the solenoid 69b is passed through the holes 621b and 681b.

The chip retracting mechanism 6b includes the solenoid 69b as a drive source for electric driving. The solenoid 69b is electrically connected to the battery 9 and the control means 11. Incidentally, the control means 11 regulates, for example, the starting timings of the operation of the pump 8 and the operation of the chip retracting mechanism 6b.

The solenoid 69b is composed of the plunger 691b and an electromagnet 692b, and the electromagnet 692b is contained in the lumen portion 63b in the state of surrounding the outer circumference of a proximal end portion of the plunger 691b.

The plunger 691b is composed of a rod-like member, and is provided with an annular flange at the distal end thereof. The distal end of the plunger 691b is attached to the proximal end of the housing 5.

When an electric current is passed to the electromagnet 692b, i.e., when the chip retracting mechanism 6b is operated, the plunger 691b is moved in the direction of the proximal end against the coil spring 67b. Since the housing 5 is attached to the distal end of the plunger 691b, the movement of the plunger 691b in the direction of the proximal end is accompanied by a movement of the housing 5 and the chip 13 mounted therein in the direction of the proximal end.

Before long, when the proximal end 591b of a projection 59b and the distal end of the wall portion 68b make contact with each other, the movement of the housing 5 and the chip 13 mounted therein in the direction of the proximal end is stopped. Therefore, by regulating the axial length of the projection 59b, it is possible to prevent the chip 13 from being spaced away from the fingertip 20 more than necessary. In other words, the projection 59b and the wall portion 68b making contact therewith constitute a means (moving distance determining means) for determining the moving distance (maximum retraction distance) of the chip 13 from the fingertip 20.

In addition, the coil spring 67b is disposed as a biasing means at the outer circumference of a distal end portion of the plunger 691b, the proximal end of the coil spring 67b is in contact with the wall portion 68b, and the distal end of the coil spring 67b is in contact with the proximal end of the housing 5. In the operating condition of the chip retracting mechanism 6b, the housing is moved in the direction of the proximal end, and the coil spring 67b is in a compressed state, thereby biasing the housing 5 in the direction of the distal end. In this case, when the passage of electric current to the electromagnet 692b is stopped (canceled), i.e., when the operation of the chip retracting mechanism 6b is canceled, the elastic force of the coil spring 67b causes the housing 5 and the chip 13 mounted therein to move in the direction of the distal end, returning to the positions where they have been before the operation of the chip retracting mechanism 6b.

With this configuration, also, the same functions and effects as those of the chip retracting mechanisms according to the first and second embodiments above can be obtained.

While the component measuring instrument according to the present invention has been described above based on the embodiments shown in the drawings, the present invention is not limited to these embodiments. For example, the configurations of the components of the component measuring instrument may be replaced by arbitrary configurations capable of displaying the same functions as above-described.

In addition, in the component measuring instrument according to the present invention, the above-described system in which the degree of coloration of the test paper caused by the reaction between a component in blood and a reagent is optically measured (calorimetry), the measurement result being converted into a measurement of the amount of the component and displayed, may be replaced by a system in which a potential variation generated according to the amount of a component in a specimen is electrically measured, and the measurement result is converted into a measurement of the amount of the component and displayed.

Besides, the operations of the pressure reducing means and the chip retracting mechanism may be started manually or may be started automatically. In the latter case, a system may be adopted in which, for example, a sensor so designed as to magnetically detect the movement of the puncture needle in the direction of the distal end at the time of puncturing the fingertip is disposed in the vicinity of a side portion of the fitting portion of the housing, and the pressure reducing means and the chip retracting mechanism are operated based on the information obtained by the sensor.

Now, the chip according to the present invention will be described below.

As has been described above, the chip according to the present invention is preferably used in the state of being mounted in the component measuring instrument according to the present invention. Since the component measuring instrument according to the present invention has been described in detail above referring to the drawings 1 to 10, the chip retracting mechanism will be briefed here, and the other items will be omitted.

Figure 11:
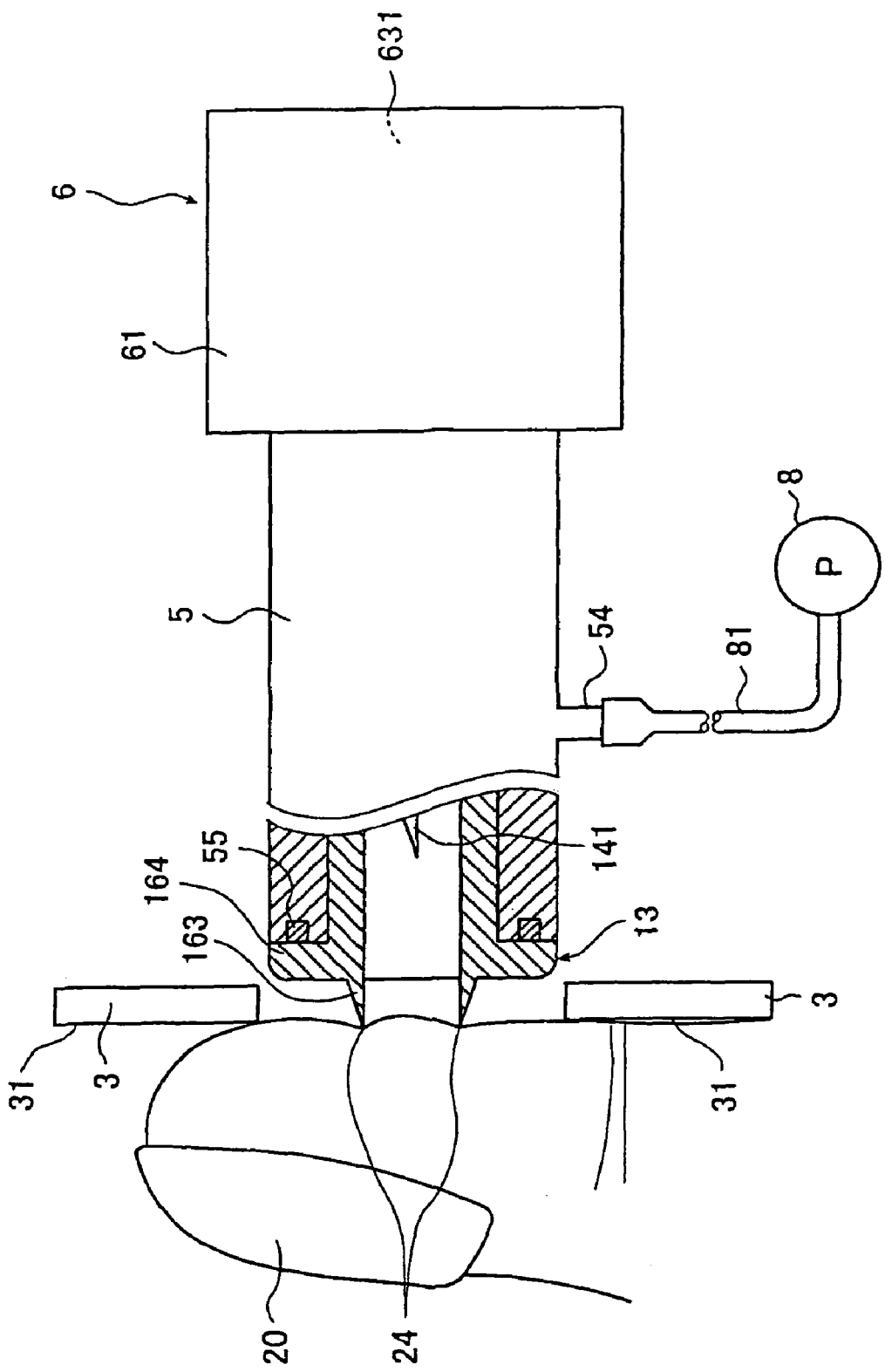
FIG. 11 is a schematic view showing the condition where a chip according to the present invention is mounted in a housing and a fingertip is in contact with the distal end of the chip.

FIG. 11 shows schematically the condition where the chip according to the present invention is mounted in a housing in the component measuring instrument and a fingertip is put in contact with the distal end of the chip. In the following description, the right side in FIG. 11 will be referred to as "the proximal end", and the left side as "the distal end".

As shown in FIG. 11, the chip retracting mechanism 6 is provided on the proximal end side of the housing 5. Incidentally, in FIG. 11, the structure of the chip 13 is shown in a simplified form.

The chip retracting mechanism 6 is for moving the housing 5 and the chip 13 mounted therein in the direction away from the fingertip 20 (in the direction of the proximal end).

The chip retracting mechanism 6 includes a main body portion 61, and a portion on the proximal end side relative to the above-mentioned flange 56 and a projection 59, of the housing 5, are contained in the main body portion 61.

In addition, a gas-tight variable-volume chamber (pressure reduction chamber) 631 is formed inside of the main body portion 61.

As has been described above, the variable-volume chamber 631 and a lumen portion 52 of the housing 5 are communicated to each other through an orifice 651 which has a high air passage resistance.

In the chip retracting mechanism 6 as above, when a pump 8 is operated in the condition where the chip 13 is mounted in the housing 5 and the fingertip 20 is kept in contact with the distal end of the chip 13 so as to seal a distal end opening 162 of the chip 13 therewith, the lumen portion 52 is first brought into a reduced-pressure condition, air inside the variable-volume chamber 631 flows through the orifice 651 into the lumen portion 52, and a reduction of the pressure inside the variable-volume chamber 631 is started. Since the orifice 651 has the high air passage resistance, the volume of the variable-volume chamber 631 gradually decreases, and the housing 5 and the chip 13 mounted therein are moved gradually in the direction away from the fingertip 20.

With the chip retracting mechanism 6 as above provided, the blood is sucked out from a punctured portion more securely and speedily.

Incidentally, in the component measuring instrument 1 in which the chip according to the present invention is mounted, the chip retracting mechanism 6 as above can be omitted, as required.

Figure 12:
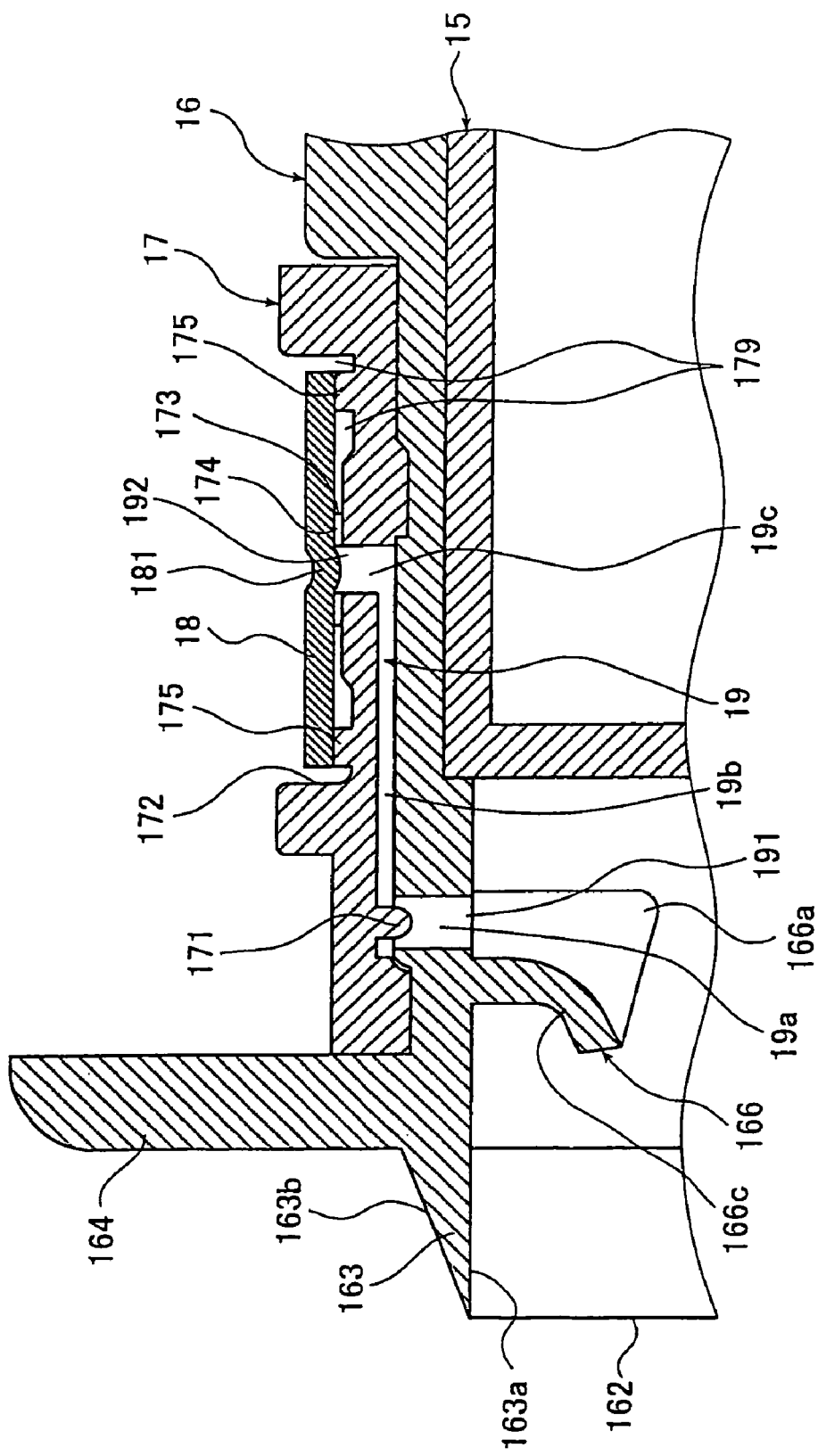
FIG. 12 is an enlarged view showing the configuration on the distal end side of a first embodiment of the chip.
Figure 13:
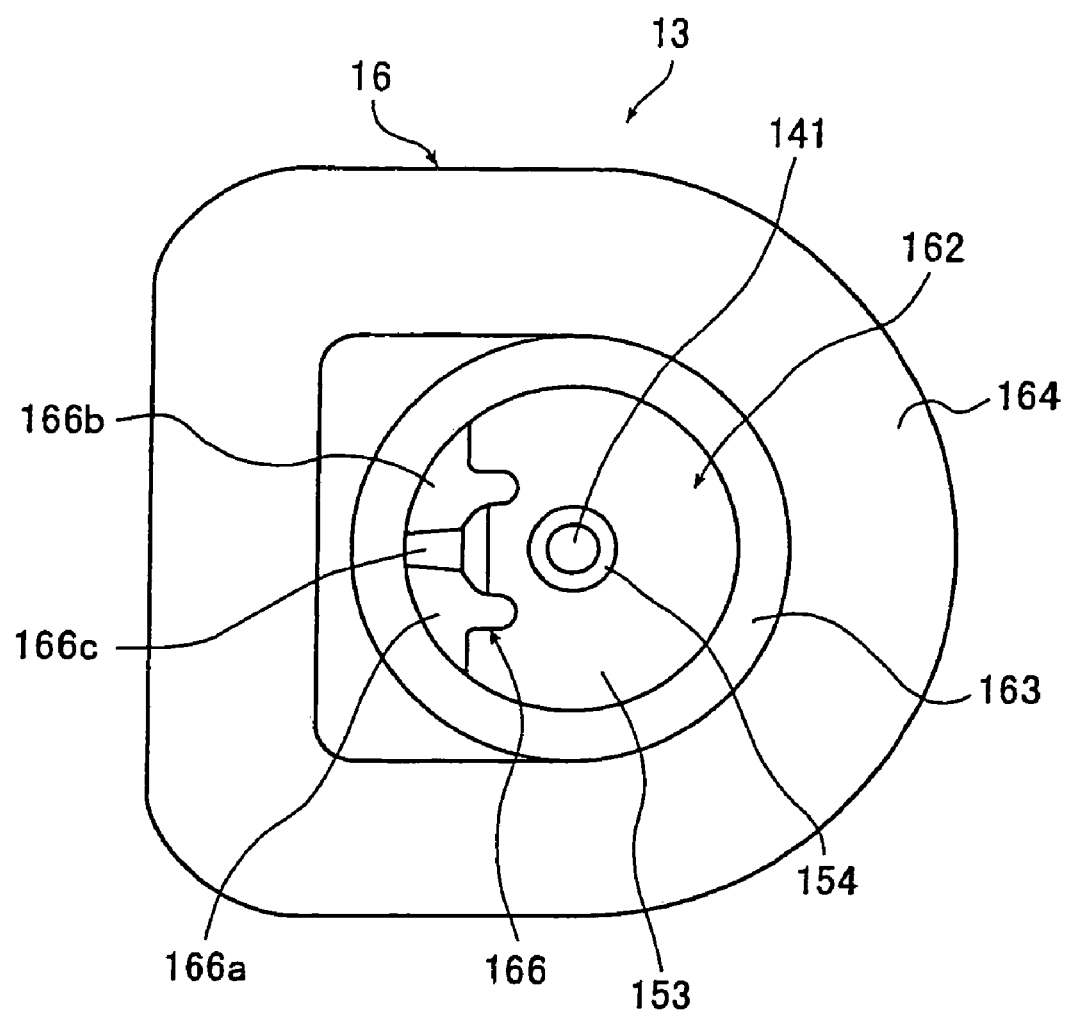
FIG. 13 is a front view of the first embodiment of the chip.
Figure 14:
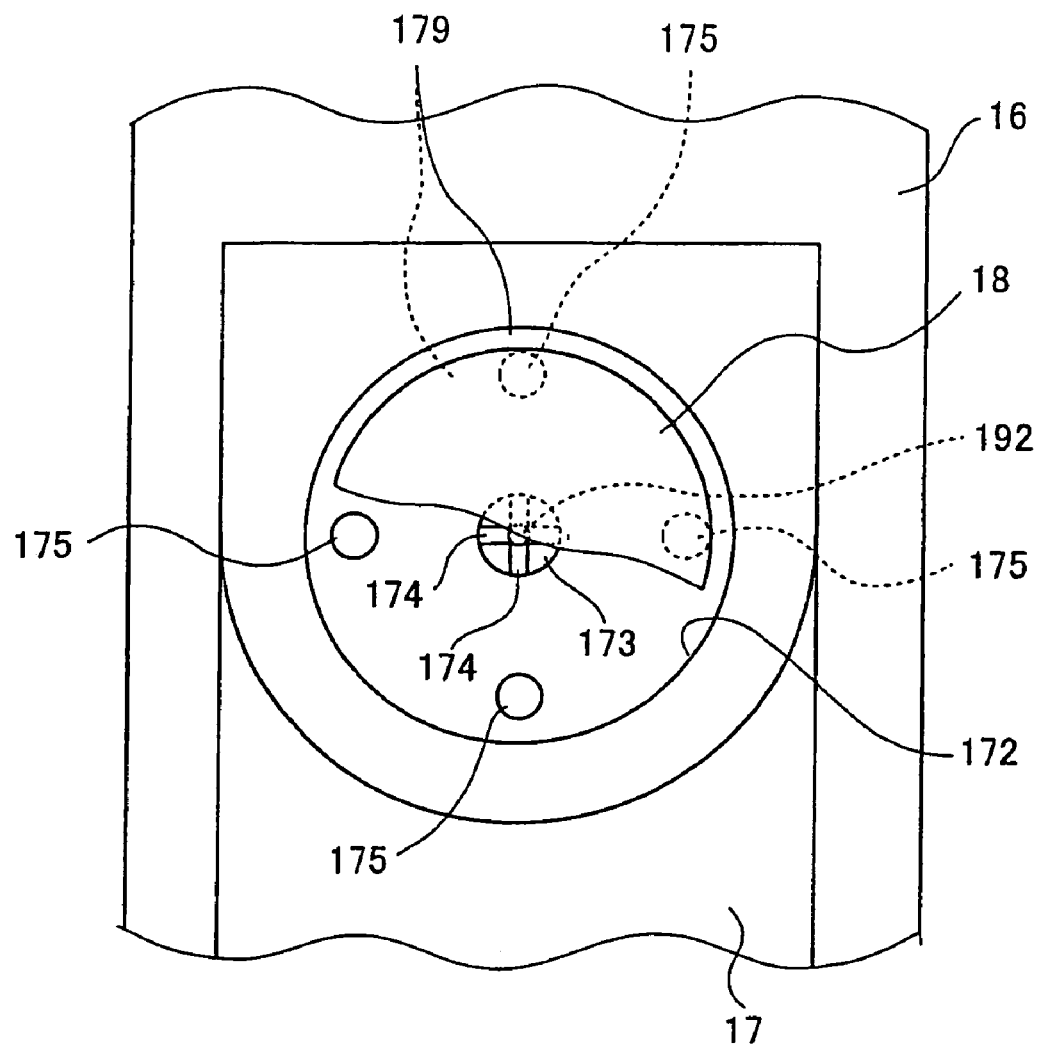
FIG. 14 is an enlarged view showing the configuration in the vicinity of a test paper fixing portion.

FIG. 2 is a vertical sectional view showing the configuration of a first embodiment of the chip, FIG. 12 is an enlarged view showing the configuration on the distal end side of the chip of the first embodiment, FIG. 13 is a front view of the chip of the first embodiment, and FIG. 14 is an enlarged view showing the configuration in the vicinity of a test paper fixing portion. In the following description, the right side in FIG. 12 will be referred to as "the proximal end", and the left side as "the distal end".

As shown in FIG. 2, the chip 13 according to this embodiment includes a puncture needle 14, a needle housing 15 for slidably containing the puncture needle 14, a chip main body 16 disposed on an outer circumferential portion of the needle housing 15, a test paper fixing portion 17 disposed at an outer circumferential portion of the chip main body 16, and a test paper 18 fixed to the test paper fixing portion 17.

The puncture needle 14 is comprised of a needle body 141, and a hub 142 attached to the proximal end side of the needle body 141, and is contained in a lumen portion 152 of the needle housing 15.

The needle body 141 is composed of a hollow member or solid member formed of a metallic material such as stainless steel, aluminum, an aluminum alloy, titanium, a titanium alloy, etc., and is provided at its distal end with a sharp needle point (knife edge). The needle point punctures the surface (skin) of the fingertip.

In addition, the hub 142 is composed of a substantially cylindrical member, and an outer circumferential portion thereof slides in contact with the inner circumferential surface 151 of the needle housing 15.

The hub 142 is provided at its proximal end portion with a reduced-diameter portion 143 which is reduced in diameter. The reduced-diameter portion 143 is fitted in a needle holder 411 of a plunger 41.

The needle housing 15 is composed of a bottomed tubular member having a wall portion 153 as a bottom portion, and the lumen portion 152 is formed inside thereof.

The wall portion 153 is provided in its roughly central portion with a hole 154 circular in sectional shape. At the time of puncturing the fingertip 20, the needle point of the needle body 141 passes through the hole 154 and through a lumen portion 161 of the chip main body 16 which will be described later. In addition, the diameter of the hole 154 is set to be smaller than the outside diameter of the distal end of the hub 142. Therefore, when the puncture needle 14 is moved in the direction of the distal end of the lumen portion 152 and the distal end of the hub 142 comes into contact with the proximal end of the wall portion 153, the puncture needle 14 is prevented from moving further in the direction of the distal end.

This ensures that when the needle point of the needle body 141 is moved to a position in the vicinity of or beyond the distal end of a contact portion 163 which will be described later, the needle point is restrained from moving further in the direction of the distal end. Namely, the needle point of the needle body 141 is so set that it can move to the position in the vicinity of or beyond the distal end of the contact portion 163 described later.

Therefore, the projecting length of the needle body 141 from the distal end of the chip 13 at the time of puncturing the fingertip 20 is kept constant, and the trouble that the needle point of the needle body 141 would puncture the fingertip 20 to a depth greater than a required depth can be prevented more securely.

Besides, a mechanism for regulating the moving distance of the plunger 41 may be provided, thereby regulating the depth of puncture of the fingertip 20 by the needle point of the needle body 141.

The inner circumferential surface 151 is provided on the proximal end side thereof with a ring form projection 155 projecting inwards, and an outer circumferential portion of the hub 142 is engaged, stopped and fixed to the projection 155. Incidentally, a setting is made such that, in this condition, the needle point of the needle body 141 does not project through the hole 154. The fixing force acting between the projection 155 and the hub 142 can be set to such a level that the puncture needle 14 can be mounted into the needle holder 411 without trouble and that the fixing between the projection 155 and the hub 142 is easily canceled when a puncturing means 4 is operated.

Incidentally, the method of fixing the hub 142 and the needle housing 15 to each other is not limited to the above-mentioned. For example, there may be adopted a method in which an engaging and stopping means is provided at the inner circumferential surface 151 and/or an outer circumferential portion of the hub 142, or a frictional force acting between the inner circumferential surface 151 and an outer circumferential portion of the hub 142 is utilized (used), or the inner circumferential surface 151 and the hub 142 are weakly adhered or weakly fused to each other, or the like.

The chip main body 16 is attached to an outer circumferential portion of the needle housing 15.

The chip main body 16 is composed of a substantially cylindrical member, and the lumen portion 161 is formed inside thereof.

In addition, the chip main body 16 is provided at its distal end with the contact portion 163 which has an annular shape such as a circular ring shape and which projects in the direction of the distal end. The contact portion 163 is a portion against which the fingertip 20 is pressed, and it is provided at its distal end with a distal end opening (opening) 162 which opens the lumen portion 161.

The chip 13 is used in the condition where, with the distal end opening 162 closed by the fingertip 20, the pressure inside the lumen portion 161 is reduced by the pump 8 and the fingertip 20 is attracted onto the distal end opening 162 by suction.

The contact portion 163 includes an inner wall surface 163a inside thereof, and an outer wall surface 163b outside thereof. The inner wall surface 163a is formed to be substantially parallel to the center axis 900 of the chip main body 16. On the other hand, the outer wall surface 163b is formed to be inclined at a predetermined angle so as to come closer to the center axis 900 in the direction from the proximal end toward the distal end. Namely, the outer wall surface 163b is tapered. With the inner wall surface 163a and the outer wall surface 163b thus provided, the contact portion 163 is so formed that its thickness decreases gradually from the proximal end to the distal end, approaching substantially to zero (preferably, 0.5 mm or less, more preferably, 0.3 mm or less) at the distal end. Namely, the distal end of the contact portion 163 is sharpened.

With the distal end of the contact portion 163 formed in such a shape, the close contact property between the fingertip 20 and the distal end opening 162 is enhanced. In addition, since it is possible to restrain air from flowing in through a gap between the distal end (distal end opening 162) of the contact portion 163 and the surface of the fingertip 20 when the lumen portion 161 is in a reduced-pressure condition, the fingertip 20 can be securely attracted onto the distal end portion 162 under suction.

Furthermore, since the close contact property between the fingertip 20 and the distal end opening 162 is high, the fingertip 20 can be prevented from slipping off from the distal end opening 162, even in the case where the above-described chip retracting mechanism 6 is operated to move the chip 13 away from the fingertip 20. Therefore, the trouble that the blood sucked out from the punctured portion would scatter to contaminate the surroundings can be prevented more securely, with the result of high safety.

Paying attention to the close contact property between the fingertip 20 and the distal end opening 162, the angle formed between the inner wall surface 163a and the outer wall surface 163b in the vicinity of the distal end of the contact portion 163 (in FIG. 2, the distal end angle θ) is required only to make it possible to form a thin shape at the distal end. The distal end angle θ is preferably about 0.5 to 60°, and more preferably about 5 to 55°. With the distal end angle θ set within the range, the above-mentioned effect is displayed more conspicuously.

Besides, the larger the distal end opening 162 is, the larger the area of congestion at the fingertip 20 becomes, and the shorter the time taken to obtain a sufficient amount of blood becomes. In consideration of the sampling of blood from the fingertip 20, however, the aperture area of the distal end opening 162 is preferably about 10 to 50 mm$^2$, and more preferably about 12 to 40 mm$^2$. In addition, with the aperture area set within the range, it is also possible to enhance the close contact property between the fingertip 20 and the distal end opening 162.

In addition, the distal end shape of the contact portion 163 as above has also the function of mitigating the pain upon puncture through stimulating the surroundings of the punctured portion when the fingertip 20 is pressed against the distal end.

The chip main body 16 is provided, at the outer circumference of a distal end portion thereof, with a flange 164 projecting in a ring form for determining the position of the chip 13 relative to the housing 5 when the chip 13 is mounted in the housing 5. As shown in FIG. 2, the distal end of the contact portion 163 is so formed as to project in the direction of the distal end from the distal end surface of the flange 164.

Besides, in the condition where the chip 13 is mounted in the component measuring instrument 1 (the housing 5), the distal end of the contact portion 163 is at substantially the same position as the finger application surface 31 or is projecting slightly beyond the finger application surface 31 (see FIG. 11). Therefore, when the fingertip 20 is applied to the finger application surface 3 of the component measuring instrument 1, the surface of the fingertip 20 securely makes contact with the distal end of the contact portion 163, whereby the distal end opening 162 can be closed.

Besides, in this condition, a portion 24 of the fingertip 20 in proximity to the distal end of the contact portion 163 forming an outer circumference is not in contact with the distal end surface of the flange 164. Therefore, capillary vessels in the vicinity of the portion 24 do not receive a pressure, so that the blood flow there is prevented from being stopped. Accordingly, a sufficient amount of blood can be obtained assuredly, and measurement with high accuracy can be achieved.

The height of the contact portion 163, i.e., the length from the distal end to the proximal end of the contact portion 163 is not particularly limited. For example, the height is preferably about 0.1 to 5 mm, and more preferably about 0.3 to 3 mm.

Incidentally, while the decrease rate of the thickness of the contact portion 163 is substantially constant in the configuration shown in the figures, this configuration is not limitative. For example, a configuration in which the decrease rate varies at an intermediate portion in the axial direction, or the like may also be adopted.

In addition, it suffices for the contact portion 163 to be so shaped that at least the thickness of a distal end portion thereof decreases gradually and that the distal end thereof is sharpened, and, therefore, the shape of the contact portion 163 is not limited to the one shown in the figures. For example, a shape in which the thickness of the contact portion 163 is substantially constant over a predetermined distance (predetermined length) from the proximal end toward the distal end and the thickness decreases gradually at a distal end portion, a shape in which the thickness of the contact portion 163 increases gradually over a predetermined distance from the proximal end toward the distal end and the thickness decreases gradually at a distal end portion, or the like may also be adopted.

The chip main body 16 is provided with a recess 165 at an outer circumferential portion thereof, and the test paper fixing portion 17 with a circular disk form test paper 18 disposed thereon is mounted in the recess 165.

In addition, there is provided a blood passage (specimen passage) 19 for communication between the lumen portion 161 of the chip main body 16 and the exterior through the chip main body 16 and the test paper fixing portion 17. The blood passage 19 is for guiding the blood obtained by puncture to the test paper 18, and comprises a passage opening 191 opened into the lumen portion 161 and a passage opening 192 opened to the exterior of the chip 13. Incidentally, the passage opening 192 is located in the vicinity of a central portion of the test paper 18.

As shown in FIG. 12, the blood passage 19 is comprised of a passage 19a extending from the passage opening 191 toward the outside of the chip main body 16, a passage 19b continuous with the passage 19a and extending substantially in parallel to the center axis 900 of the chip main body 16 toward the proximal end side, and a passage 19c continuous with the passage 19b and extending toward the outside of the chip main body 16 to the passage opening 192. The passages 19a and 19c are connected to and substantially orthogonal to the passage 19b.

The blood passage 19 as above can be formed, for example, by molding, processing and joining the chip main body 16 and the test paper fixing portion 17.

The blood passage 19 is formed to be substantially rectangular in sectional shape, to have a thickness of preferably about 0.05 to 0.5 mm, for example, and to have a width of preferably about 0.5 to 3 mm, for example. Incidentally, the shape of the blood passage 19 can be appropriately selected according to the blood amount (specimen amount) necessary for measurement. It suffices for the shape of the blood passage 19 to be so designed that the amount of blood left inside thereof can be reduced. For example, the sectional shape of the blood passage 19 may also be tubular, U-shaped, V-shaped, or the like.

Meanwhile, in the condition where the chip 13 is mounted in the housing 5, the test paper 18 is disposed on the chip main body 16 so as to be located in the vicinity of a side portion of the measuring means 7. Specifically, the position of the test paper 18 relative to the chip 13 is set according to the installation position of the measuring means 7 in the component measuring instrument 1, and the length of the blood passage 19 is also set accordingly. Therefore, the length of the blood passage 19 is appropriately selected according to the installation position of the measuring means 7 in the component measuring instrument 1, and is not particularly limited; normally, the length is preferably about 5 to 15 mm. With the length of the blood passage 19 set within the range, blood can be guided to the test paper 18 more speedily and securely.

The chip main body 16 is provided on its inner circumferential surface with a blood introducing guide 166 projecting into the lumen portion 161. The blood introducing guide 166 has the function of making contact with the blood rising in a grain form on the punctured portion toward the lumen portion 161, upon puncture of the fingertip 20, and receiving (introducing) the blood.

As shown in FIG. 13, the blood introducing guide 166 is comprised of a pair of wall portions 166a and 166b and a distal end wall portion 166c, and is so formed as to surround the three sides of the passage opening 191. Therefore, the blood received by the blood introducing guide 166 is efficiently guided from the passage opening 191 into the blood passage 19.

Furthermore, the wall portions 166a and 166b are so formed that their opposed surfaces are spaced farther away from each other as the center axis 900 of the chip main body 16 is approached. Namely, the wall portions 166a and 166b are so formed as to be opened nearly in an inverted V shape. With the blood introducing guide 166 configured in this manner, it is possible to receive the blood more securely and to guide the blood into the blood passage 19 more securely and speedily.

As for the size of the space defined by the wall portion 166a, the wall portion 166b and the distal end wall portion 166c of the blood introducing guide 166 as above, it is preferable that the width (in FIG. 13, the length in the vertical direction) is about 1 to 3 mm, the height (in FIG. 13, the length in the lateral direction) is about 0.5 to 3 mm, and the length (in FIG. 13, the length in the direction orthogonal to the paper surface) is about 1 to 3 mm.

Incidentally, the shape of the blood introducing guide 166 is not limited to the one shown in the figure, inasmuch as the blood introducing guide 166 can securely receive the blood and can guide the blood into the blood passage 19 securely and speedily. For example, a shape in which the wall portions 166a and 166b are substantially parallel to each other, a shape in which a proximal end wall portion is provided so as to surround the four sides of the passage opening 191, or the like may also be adopted.

The test paper fixing portion 17 is provided on its lower surface with a projection 171 projecting toward the inside of the passage 19a. With the projection 171 thus provided, generation of a meniscus in the blood passage 19 can be suppressed. In addition, the test paper 18 is provided, in the vicinity of a central portion thereof, with a projection 181 projecting toward the inside of the passage 19c; the projection 181 produces the same effect as that of the projection 171. This makes it possible to guide the blood to the test paper 18 more speedily and securely.

As shown in FIGS. 12 and 14, the test paper fixing portion 17 is provided at its upper surface with a recess 172 corresponding to the shape of the test paper 18. In addition, at the bottom surface of the recess 172, there are provided a mount portion 173 raised so as to surround the perimeter of the passage opening 192, and a plurality of mount portions (in this embodiment, four mount portions at an angular interval of 90°) 175 raised with the mount portion 173 as a center. The test paper 18 is fixed to the mount portions 173 and 175 by a method such as fusing, adhesion with an adhesive, etc.

In the condition where the test paper 18 is disposed on the test paper fixing portion 17, gaps 179 are formed between the outer circumferential edge portion of the test paper 18 and the inner circumferential surface of the recess 172, and between the lower surface of the test paper 18 and the bottom surface of the recess 172.

Besides, the mount portion 173 is provided with a groove 174 communicated with the blood passage 19. In the configuration shown in the figure, the groove 174 is in the shape of a cross. The outside end portions of the groove 174 are each opened to the outer circumferential surface of the mount portion 173. That is, the blood passage 19 and the gap 179 are communicated with each other through the groove 174.

The groove 174 and the gap 179 as above function as air vents for the blood passage 19, whereby the blood can be prevented from stopping at an intermediate portion of the blood passage 19.

In addition, the gap 179 has the function of assisting (promoting) the development of blood on the test paper 18. To be more specific, the blood having passed through the blood passage 19 spreads from the passage opening 192 in the direction of the outer circumference through the groove 174, whereby the blood is supplied to and radially developed on the test paper 18, so that the development of the blood on the test paper 18 can be achieved speedily and uniformly.

The hub 142, the needle housing 15, the chip main body 16 and the test paper fixing portion 17 as above-described are each preferably formed of a resin material. Examples of the resin material include thermoplastic resins ordinarily used in injection molding, such as ABS resin, AS resin, polyethylene, polypropylene, polystyrene, polyvinyl chloride, polyvinylidene chloride resin, polyphenylene oxide, thermoplastic polyurethane, polymethylene methacrylate, polyoxyethylene, fluororesin, polycarbonate, polyamide, acetal resin, acrylic resin, polyethylene terephthalate, etc., and thermosetting resins such as phenol resin, epoxy resin, silicone resin, unsaturated polyester, etc. Particularly, the chip main body 16 and the test paper fixing portion 17 are each preferably formed of a highly hydrophilic resin such as acrylic resin or a resin treated to be hydrophilic, since such a hydrophilic resin is particularly suitable for speedy introduction and development of blood.

The treatment for rendering a resin hydrophilic can be conducted, for example, by a physical activating treatment such as ozone treatment, plasma treatment, glow discharge, corona discharge, irradiation with UV rays, etc., or by application of (coating with) a surface active agent, a water-soluble silicone, hydroxypropyl cellulose, polyethylene glycol, polypropylene glycol, or the like.

The test paper 18 is composed of a circular disk form member, and is provided with a projection 181 in the vicinity of a central portion thereof, as described above. The tip end of the projection 181 projects toward the inside of the blood passage 19 (passage 19c). This makes it possible to support and fix the test paper 18 onto the test paper fixing portion 17 more stably, and to prevent the trouble in which uniform development of blood would be hindered by deformation (curvature, distortion, undulation, etc.) of the test paper 18.

Incidentally, the shape of the test paper 18 in plan view is not limited to the circular shape (circular disk shape) as shown in the figure. For example, a shape appropriately selected from ellipses; tetragons such as square, rectangle, rhombus, etc.; triangles; hexagons; octagons, etc. may be adopted, as required.

In the case of the circular disk form test paper 18, the outside diameter of the test paper 18 is preferably about 3 to 8 mm, and the thickness of the test paper 18 is preferably about 0.05 to 0.4 mm.

The test paper 18 as above is comprised of a carrier capable of absorbing and developing the blood (specimen), and a reagent carried on the carrier. The kind of the carrier and the reagent to be carried on the carrier are the same as those in the case of a general chip for use in the component measuring instrument according to the present invention, and, therefore, description thereof is omitted.

Now, a second embodiment of the chip according to the present invention will be described below.

Figure 15:
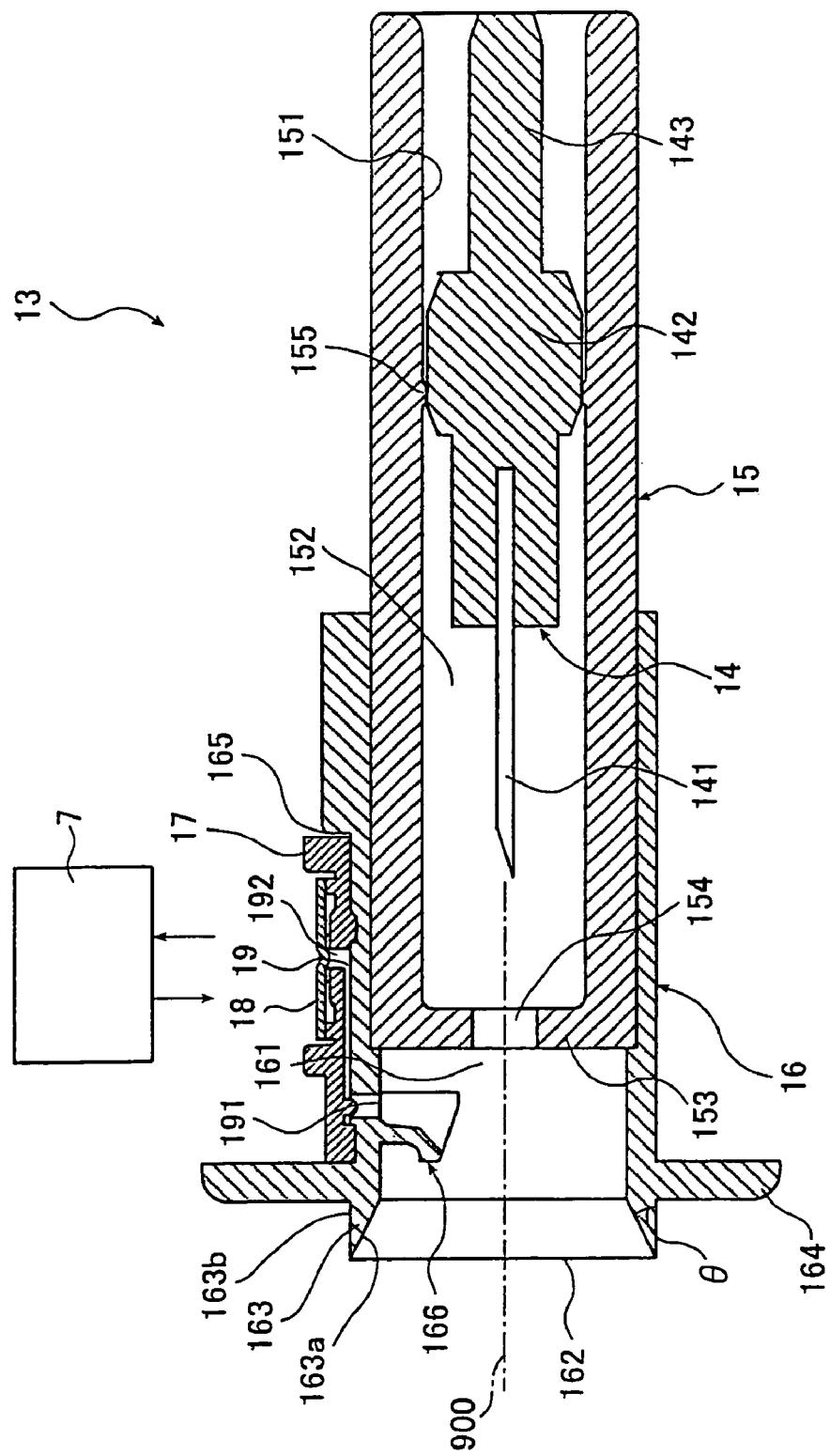
FIG. 15 is a vertical sectional view showing the configuration of a second embodiment of the chip.

FIG. 15 is a vertical sectional view showing the configuration of the second embodiment of the chip.

Description of the second embodiment of the chip shown in FIG. 15 will be made centering on the difference thereof from the first embodiment above, and the same items as those in the first embodiment will be omitted. In the following description, the right side in FIG. 15 will be referred to as "the proximal end", and the left side as "the distal end".

In the second embodiment of the chip, the shape of a contact portion 163 is different from that in the first embodiment. Specifically, an outer wall surface 163b is formed to be substantially parallel to the center axis 900 of a chip main body 16. On the other hand, an inner wall surface 163a is formed to be inclined at a predetermined angle so as to be spaced farther away from the center axis 900 in the direction from the proximal end toward the distal end. Namely, the inner wall surface 163a is tapered. With the inner wall surface 163a and the outer wall surface 163b thus formed, the contact portion 163 gradually decreases in thickness from the proximal end toward the distal end thereof, and is sharpened at the distal end thereof.

With this configuration, also, the same effects as those in the above-described first embodiment of the chip can be obtained.

Now, a third embodiment of the chip according to the present invention will be described below.

Figure 16:
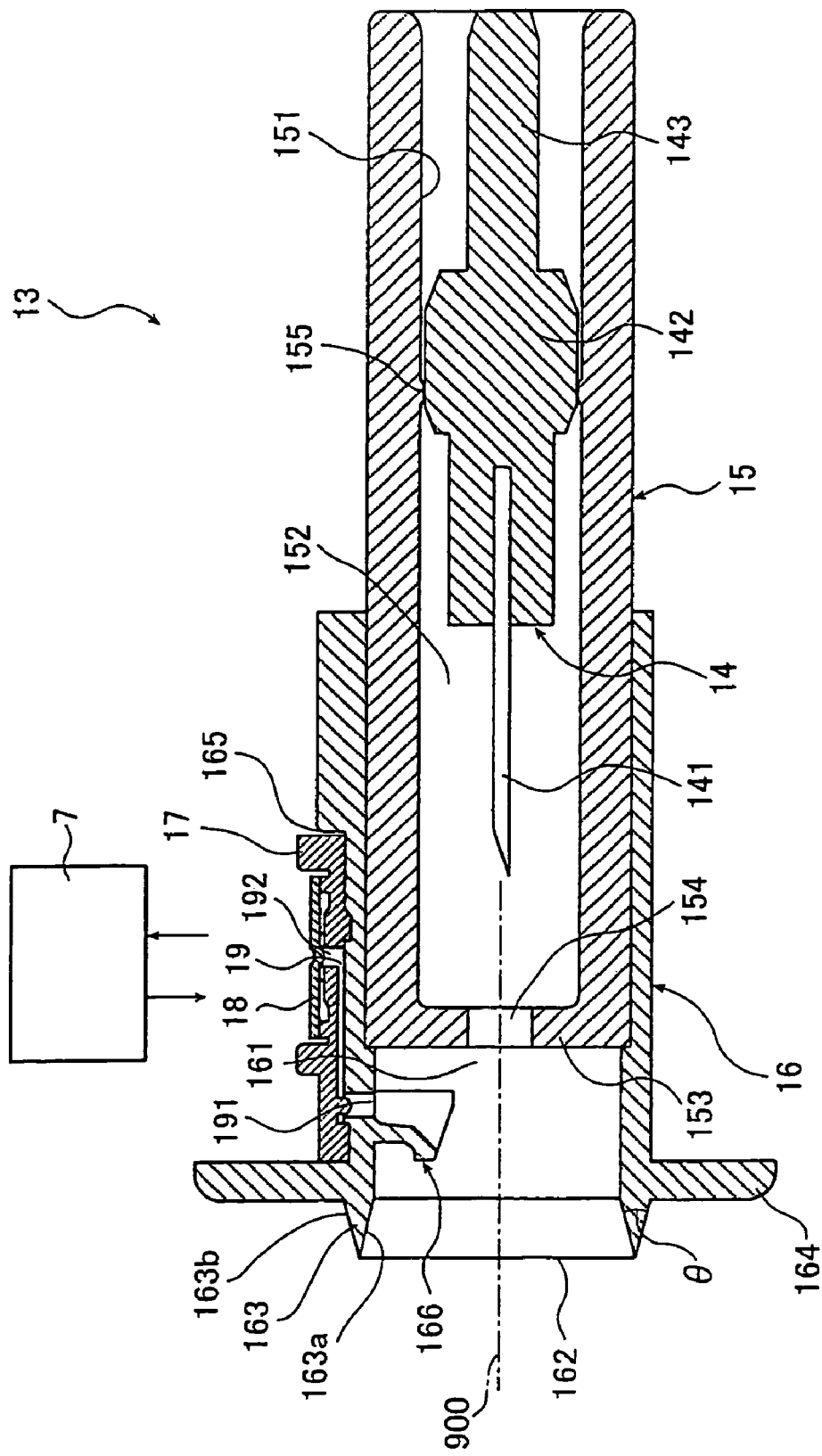
FIG. 16 is a vertical sectional view showing the configuration of a third embodiment of the chip.

FIG. 16 is a vertical sectional view showing the configuration of the third embodiment of the chip.

Description of the third embodiment of the chip shown in FIG. 16 will be made centering on the difference thereof from the first embodiment above, and description of the same items as those in the first embodiment will be omitted. In the following description, the right side in FIG. 16 will be referred to as "the proximal end", and the left side as "the distal end".

In the third embodiment of the chip, the shape of a contact portion 163 is different from that in the first embodiment. Specifically, an inner wall surface 163a is formed to be inclined at a predetermined angle so as to be spaced farther away from the center axis 900 in the direction from the proximal end toward the distal end. On the other hand, an outer wall surface 163b is formed to be inclined at a predetermined angle so as to gradually approach the center axis 900 in the direction from the proximal end toward the distal end. Namely, the inner wall surface 163a and the outer wall surface 163b are tapered so that they gradually approach each other in the direction from the proximal end toward the distal end.

This ensures that the contact portion 163 gradually decreases in thickness from the proximal end toward the distal end thereof, and is sharpened at the distal end thereof.

With this configuration, also, the same effects as those of the above-described first embodiment of the chip can be obtained.

Now, a fourth embodiment of the chip according to the present invention will be described below.

Figure 17:
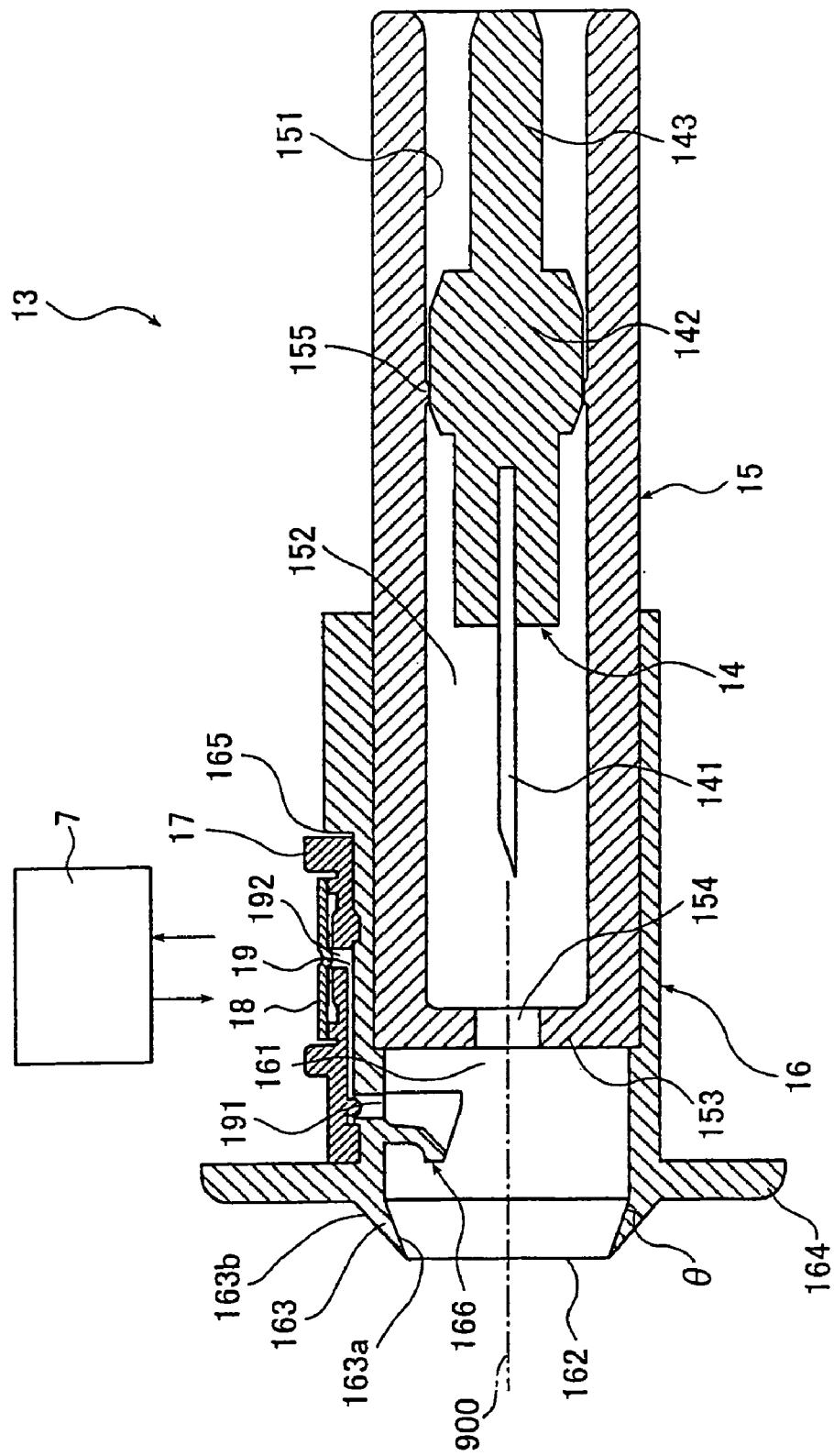
FIG. 17 is a vertical sectional view showing the configuration of a fourth embodiment of the chip.

FIG. 17 is a vertical sectional view showing the configuration of the fourth embodiment of the chip.

Description of the fourth embodiment of the chip shown in FIG. 17 will be made centering on the difference thereof from the first embodiment above, and description of the same items as those in the first embodiment will be omitted. In the following description, the right side in FIG. 17 will be referred to as "the proximal end", and the left side as "the distal end".

In the fourth embodiment of the chip, the shape of a contact portion 163 is different from that in the first embodiment. Specifically, an inner wall surface 163a and an outer wall surface 163b are formed to be inclined respectively at predetermined angles so as to gradually approach the center axis 900 of a chip main body 16 in the direction from the proximal end toward the distal end. Namely, the inner wall surface 163a and the outer wall surface 163b are individually tapered. In addition, the angle between the outer wall surface 163b and the center axis 900 is set to be greater than the angle between the inner wall surface 163a and the center axis 900. This ensures that the contact portion 163 gradually decreases in thickness from the proximal end toward the distal end thereof, and is sharpened at the distal end thereof.

With this configuration, also, the same effects as those in the above-described first embodiment of the chip can be obtained.

Besides, in the chip thus configured, there is the merit that the diameter of a distal end opening 162 can be set to be smaller than the diameter of a lumen portion 161 of the chip main body 16. Therefore, the chip thus configured is suitable for use for infants, for example.

Now, a fifth embodiment of the chip according to the present invention will be described below.

Figure 18:
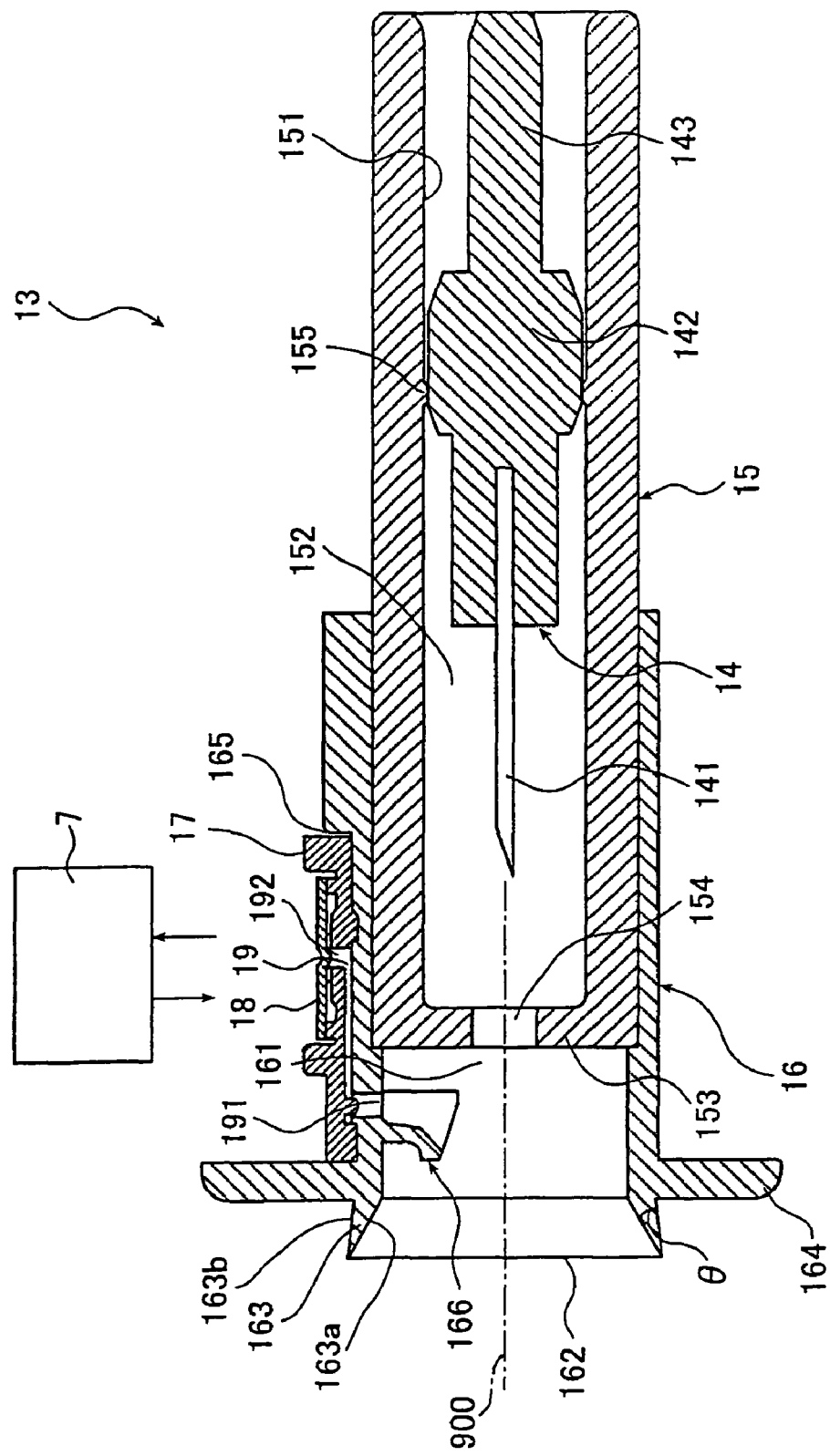
FIG. 18 is a vertical sectional view showing the configuration of a fifth embodiment of the chip.

FIG. 18 is a vertical sectional view showing the configuration of the fifth embodiment of the chip.

Description of the fifth embodiment of the chip shown in FIG. 18 will be made centering on the difference thereof from the first embodiment, and description of the same items as those in the first embodiment will be omitted. In the following description, the right side in FIG. 18 will be referred to as "the proximal end", and the left side as "the distal end".

In the fifth embodiment of the chip, the shape of a contact portion 163 is different from that in the first embodiment. Specifically, an inner wall surface 163a and an outer wall surface 163b are formed to be inclined at predetermined angles so as to be spaced farther away from the center axis 900 of a chip main body 16 in the direction from the proximal end toward the distal end. Namely, the inner wall surface 163a and the outer wall surface 163b are individually tapered. In addition, the angle between the inner wall surface 163a and the center axis 900 is set to be greater than the angle between the outer wall surface 163b and the center axis 900. This ensures that the contact portion 163 gradually decreases in thickness from the proximal end toward the distal end thereof, and is sharpened at the distal end thereof.

With this configuration, also, the same effects as those in the above-described first embodiment can be obtained.

Besides, in the chip thus configured, there is the merit that the diameter of a distal end opening 162 can be set to be greater than the diameter of a lumen portion 161 of the chip main body 16. Therefore, the chip thus configured is suitable for use for specimen sampling portions other than a fingertip, such as an earlobe, an abdominal portion, a thigh, an arm, etc.

While the chip according to the present invention has been described above based on the embodiments shown in the drawings, the present invention is not limited to the embodiments. For example, the configurations of the components of the chip may be replaced by arbitrary configurations capable of displaying the same functions as above-described.

While blood has been taken as the specimen in the above descriptions of the component measuring instrument according to the present invention and the chip according to the present invention, the specimen is not limited to blood. Other than blood, the specimen may, for example, be a body fluid such as urine, lymph fluid, spinal fluid, bile, saliva, etc. or a diluted or concentrated liquid thereof.

In addition, while a fingertip has been described as a representative of the specimen sampling portion, the specimen sampling portion is naturally not limited to the fingertip, as mentioned above.

Moreover, the component to be measured is not limited to glucose (blood sugar). The component to be measured may, for example, be proteins, cholesterol, uric acid, creatinine, alcohol, an inorganic ion such as sodium, hemoglobin (occult blood), or the like.

INDUSTRIAL APPLICABILITY

As has been described above, according to the component measuring instrument of the present invention, it is possible to provide a component measuring instrument capable of measuring a predetermined component in blood more securely and in a short time.

With the chip retracting mechanism provided, a bleeding amount can be secured sufficiently, and measurement with higher accuracy can be achieved, without mistakes in measurement.

In addition, if the test paper is provided on the chip, puncture, sampling of a body fluid, development of the body fluid onto the test paper, and measurement (quantifying of the component) can be performed continuously, and the component measurement can be achieved easily and in a short time.

Besides, since a preparatory operation for use is easy, the component measuring instrument is advantageous also in the case of periodic use and in the case of repeated use.

Furthermore, accidents such as mistaken re-puncturing of the surface of an organism after puncture can be prevented, and high safety is secured, Moreover, since the puncture needle is not seen directly to the patient, the fear at the time of puncture is alleviated.

From the foregoing, the component measuring instrument according to the present invention is suitable for use in the case where blood sugar or the like of the patient is measured by the patient himself.

Besides, the component measuring instrument according to the present invention is simple in configuration, is small in size and weight, is inexpensive, and is suitable for mass production.

In addition, according to the chip of the present invention, in the case where the specimen sampling portion is a fingertip, for example, the close contact property between the chip and the fingertip is enhanced, and blood flow can be prevented from being stopped, so that blood can be sampled more securely.

Besides, with the distal end of the contact portion formed in a sharpened shape, the close contact property between the distal end and the fingertip is enhanced, and the above-mentioned effect is displayed more conspicuously.

With the chip as above-described, in the case where the chip is used with its lumen portion in a reduced-pressure condition, the fingertip can be attracted by suction more securely, and blood (specimen) can be sampled more securely and speedily.

In addition, if the chip is provided with the puncture needle and the test paper, puncture, sampling of blood, development of the blood onto the test paper, and measurement (quantifying of a component) can be performed continuously, and component measurement can be achieved easily and in a short time.

Besides, in use of the chip, an operation (preparatory operation) of mounting the chip into the component measuring instrument, for example, is easy and, therefore, the chip is advantageous also in the case of periodic use and in the case of repeated use.

As seen from the foregoing, the chip according to the present invention is suitable also for use in the case where blood sugar or the like of the patient is measured by the patient himself, and the chip promises measurement with high accuracy.

The invention claimed is:

1. A component measuring instrument used by mounting therein a chip comprising a puncture needle and a contact portion for making contact with a specimen sampling portion, comprising:
   a specimen sampling portion application portion which is capable of having a specimen sampling portion to be punctured applied thereon;
   puncturing means for moving said puncture needle to puncture the specimen sampling portion applied onto said specimen sampling portion application portion;
   pressure reducing means for putting the punctured portion of the specimen sampling portion punctured by said puncture needle, together with a containing space for said puncture needle, into a reduced-pressure condition;
   measuring means for measuring the amount of a predetermined component in a blood sample from the punctured portion; and
   a chip retracting mechanism for moving said chip, including said puncture needle and said contact portion, in a direction away from the specimen sampling portion, said contact portion being kept in contact with a surface of the specimen sampling portion as said chip moves in said direction so as to maintain said reduced-pressure condition generated by said pressure reducing means.

2. The component measuring instrument as set forth in claim 1, wherein the movement of said chip is carried out on the basis of said puncturing means in the condition where said chip is attached to said puncturing means.

3. The component measuring instrument as set forth in claim 1, wherein said chip retracting mechanism is operated by utilizing a pressure reducing force generated by the operation of said pressure reducing means.

4. The component measuring instrument as set forth in claim 3, wherein
   said chip retracting mechanism comprises a pressure reduction chamber, and at least one passage having a high air passage resistance for communication between said pressure reduction chamber and said containing space, and
   the pressure inside said pressure reduction chamber is reduced through said passage, thereby moving said chip in a direction away from the specimen sampling portion application portion.

5. The component measuring instrument as set forth in claim 1, wherein said chip retracting mechanism has a drive source for electric driving, and said chip retracting mechanism is operated by the driving of said drive source.

6. The component measuring instrument as set forth in claim 5, wherein said drive source is a solenoid.

7. The component measuring instrument as set forth in claim 1, wherein said chip retracting mechanism has biasing means such that said chip is returned to a previous position by said biasing means when the operation of said chip retracting mechanism is canceled.

8. The component measuring instrument as set forth in claim 1, wherein
   said component measuring instrument comprises a housing for holding said chip and incorporating said puncturing means therein, and
   said pressure reducing means puts said containing space in the housing into a reduced-pressure condition.

9. The component measuring instrument as set forth in claim 1, wherein the operation of said puncturing means and the operation of said pressure reducing means can be started substantially simultaneously.

10. The component measuring instrument as set forth in claim 1, wherein said chip retracting mechanism is operated in succession to the operation of said pressure reducing means.

11. The component measuring instrument as set forth in claim 1, comprising moving distance determining means for determining the distance of movement of said chip by said chip retracting mechanism.

12. The component measuring instrument as set forth in claim 1, wherein said contact portion includes an opening provided on the inside of said contact portion such that, when in use, said opening is capable of being closed by the specimen sampling portion.

13. The component measuring instrument as set forth in claim 12, wherein
    said specimen sampling portion application portion has a specimen sampling portion application surface, and
    the distal end of said contact portion is located at substantially the same horizontal plane as said specimen sampling portion application surface or slightly projecting from the horizontal plane of said specimen sampling portion application surface, in the condition where said chip is mounted in said component measuring instrument.

14. The component measuring instrument as set forth in claim 1, wherein said chip comprises a test paper, and a blood passage for supplying blood to said test paper.

15. The component measuring instrument as set forth in claim 14, wherein said test paper is a test paper for blood sugar measurement.

16. The component measuring instrument as set forth in claim 1, wherein said chip comprises:
    a chip main body having a lumen portion; and
    said contact portion defines an annularly projecting contact portion which is formed at the distal end of said chip main body and which is adapted to be brought into contact with the specimen sampling portion, wherein
    at least a distal end portion of said contact portion decreases in thickness gradually along the direction from the proximal end toward the distal end thereof.

* * * * *